(12) United States Patent
Mochly-Rosen et al.

(10) Patent No.: US 7,851,587 B2
(45) Date of Patent: Dec. 14, 2010

(54) PEPTIDES DERIVED FROM THE C2 DOMAIN OF EPSILON PKC

(75) Inventors: Daria D. Mochly-Rosen, Melo Park, CA (US); Relly Brandman, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 306 days.

(21) Appl. No.: 11/906,645

(22) Filed: Oct. 2, 2007

(65) Prior Publication Data

US 2009/0075897 A1    Mar. 19, 2009

Related U.S. Application Data

(60) Provisional application No. 60/849,163, filed on Oct. 2, 2006, provisional application No. 60/873,482, filed on Dec. 6, 2006.

(51) Int. Cl.
  *C07K 7/06* (2006.01)
  *A61K 39/385* (2006.01)

(52) U.S. Cl. .................... 530/300; 530/328; 530/329; 530/330; 424/193.1

(58) Field of Classification Search .............. None
  See application file for complete search history.

(56) References Cited

U.S. PATENT DOCUMENTS

| 5,478,810 | A | * | 12/1995 | Stuber et al. | 514/17 |
| 5,776,716 | A | * | 7/1998 | Ron et al. | 435/15 |
| 5,935,803 | A | * | 8/1999 | Vasquez et al. | 435/15 |
| 6,683,052 | B1 | * | 1/2004 | Thiam et al. | 514/12 |
| 6,933,275 | B2 | * | 8/2005 | Mochly-Rosen et al. | 514/2 |

FOREIGN PATENT DOCUMENTS

| WO | WO98/17299 A1 | 4/1998 |
| WO | WO02/057413 A2 | 7/2002 |
| WO | WO02/057413 A3 | 7/2002 |
| WO | WO02/078600 A2 | 10/2002 |
| WO | WO02/078600 A3 | 10/2002 |
| WO | WO2005/025602 A1 | 3/2005 |
| WO | WO2005/059124 A2 | 6/2005 |
| WO | WO2005/059124 A3 | 6/2005 |

OTHER PUBLICATIONS

Theodore et al (J. Neurosci. 15: 7158-7167, 1995).*
The International Search Report and Written Opinion for PCT Application No. PCT/US2007/021276, search report dated Jul. 22, 2008, 16 pages (2008).
Begley, R., Liron, T., Baryza, J., and Mochly-Rosen, D., *Biochem Biophys Res Commun.*, 318:949-54 (2004).
Chen, L., Hahn, H., Wu, G., Chen, C. H., Liron, T., Schechtman, D., Cavallaro, G., Banci, L., Guo, Y., Bolli, R., Dorn, G. W., 2nd, and Mochly-Rosen, D., *Proc Natl Acad Sci U S A*, 98(20):11114-11119 (2001).
Dorn, G. W., 2nd, Souroujon, M. C., Liron, T., Chen, C. H., Gray, M. O., Zhou, H. Z., Csukai, M., Wu, G., Lorenz, J. N., and Mochly-Rosen, D. *Proc Natl Acad Sci U S A* 96(22):12798-12803 (1999).
Gray, M. O., Karliner, J. S., and Mochly-Rosen, D., *J Biol Chem.* ,272(49):30945-30951 (1997).
Inagaki, K., Hahn, H. S., Dorn, G. W. and Mochly-Rosen, D., *Circulation*, 108:869-875 (2003).
Johnson, J. A., Gray, M. O., Chen, C. H., and Mochly-Rosen, D., *J Biol Chem* 271(40):24962-24966 (1996).
Johnson, J.A., Gray, M.O., Karliner, J.S., Chen, C.H., and Mochly-Rosen, D., *Circ. Res.*, 79:1086-99 (1996).
Koponen, S., Kurkinen, K., Akerman, K. E., Mochly-Rosen, D., Chan, P. H., and Koistinaho, J., *J Neurochem.*, 86:442-450 (2003).
Ron, D., Luo, J., and Mochly-Rosen, D., *J Biol Chem.*, 270:24180-24187 (1995).
Saurin, A. T., Pennington, D. J., Raat, N. J., Latchman, D. S., Owen, M. J., and Marber, M. S., *Cardiovasc Res.*, 55:672-680 (2002).
Smith, B. L., and Mochly-Rosen, D., *Biochem Biophys Res Commun.*, 188(3):1235-1240 (1992).
Souroujon, M. C., and Mochly-Rosen, D., *Nat Biotechnol.*, 16:919-924 (1998).
Sweitzer, S. M., Wong, S. M., Peters, M. C., Mochly-Rosen, D., Yeomans, D. C., and Kendig, J. J., *J Pharmacol Exp Ther.*, 309(2):616-625 (2004).
Yedovitzky, M., Mochly-Rosen, D., Johnson, J. A., Gray, M. O., Ron, D., Abramovitch, E., Cerasi, E., and Nesher, R., *J Biol Chem.*, 272(3):1417-1420 (1997).
Zhang, Z. H., Johnson, J. A., Chen, L., El-Sherif, N., Mochly-Rosen, D., and Boutjdir, M., *Circ Res.*, 80:720-729 (1997).

* cited by examiner

*Primary Examiner*—Robert Landsman
*Assistant Examiner*—Gyan Chandra
(74) *Attorney, Agent, or Firm*—King & Spalding LLP; Judy Mohr; Susan Harlocker

(57) ABSTRACT

Peptides derived from the C2 regions of εPKC and methods of use, thereof, are described. These peptides modulate the activity of εPKC in an animal model of acute ischemic heart disease.

22 Claims, 7 Drawing Sheets

US 7,851,587 B2

PEPTIDES DERIVED FROM THE C2 DOMAIN OF EPSILON PKC

CROSS-REFERENCE TO RELATED APPLICATIONS

This application claims the benefit of U.S. Provisional Application No. 60/849,163, filed Oct. 2, 2006; U.S. Provisional Application No. 60/873,482, filed Dec. 6, 2006, all of which are incorporated herein by reference in its entirety.

FEDERALLY-SPONSORED RESEARCH OR DEVELOPMENT

This invention was made with Government support under contract HL052141 awarded by the National Institutes of Health. The Government has certain rights in this invention.

TECHNICAL FIELD

The subject matter described herein relates to peptides derived from regions of the PKC polypeptide spanning the C2 domain. The peptides modulate the activity of PKC and are useful for reducing the severity of, e.g., acute ischemic heart disease and stroke.

BACKGROUND

Protein kinase C (PKC) enzymes are a family of serine and threonine protein kinases involved in apoptosis (14,15), cell proliferation (16-18), secretion (19), and disease states, including ischemic heart disease (4, 20-22) and stroke (23, 24). PKC activation involves binding to negatively charged phospholipids and phosphatidylserine. Different PKC isozymes have different sensitivities to other modulators, including $Ca^{2+}$ and lipid-derived second messengers, such as diacylglycerol (25). Following activation by one or more binding events, PKC isozymes are known to translocate from the soluble cell fraction to the particulate cell fraction (26) containing cell membranes, nuclei, mitochondria, and other components (27,28).

The primary amino acid sequence of PKC can generally be separated into two domains: (i) the N-terminal regulatory domain and (ii) the conserved C-terminal catalytic domain. The regulatory domain includes the C1 and C2 domains, which mediate interactions with second messengers and phospholipids, and generally modulate inter and intramolecular protein-protein interactions. Differences in the primary amino acid sequence, order, and number of copies of signaling domains, contribute to the different activity and/or specificities of different PKC isozymes (25,30). C2 domains in at least one PKC subfamily were called region "V1" until homology to the C2 domains of other family members was recognized (29).

A small region of the C2 domain has been shown to modulate protein-protein interactions (2,5). In particular, several peptides derived from a region of the C2 domain were shown to act as competitive inhibitors of PKC (1). A peptide that interfered with interactions between εPKC and its anchoring protein, εRACK, inhibited εPKC activity (5). A peptide the interfered with auto-inhibitory intramolecular interactions increased PKC activity and reduced ischemic death in an animal model for ischemic heart disease (4,5,7). Related 6-10 amino acid peptides from the same region of C2 were identified (5,22,31-34) and shown to be selective and effective in regulating the biological activities of the corresponding PKC isozymes.

Such studies are limited to a small region of the C2 domain. The need exists to identify other regions of the C2 domain that modulate PKC activity, and to develop selective peptide inhibitors based on such regions. Such peptides are candidates for drug development (6,9,10,12,18,23,28,35-41).

REFERENCES

The following references, as well as additional reference cited in the text, are hereby incorporated by reference in their entirety.

1. Souroujon, M. C., and Mochly-Rosen, D. (1998) *Nat Biotechnol* 16, 919-924
2. Smith, B. L., and Mochly-Rosen, D. (1992) *Biochem Biophys Res Commun* 188, 1235-1240
3. Yedovitzky, M., Mochly-Rosen, D., Johnson, J. A., Gray, M. O., Ron, D., Abramovitch, E., Cerasi, E., and Nesher, R. (1997) *J Biol Chem* 272, 1417-1420
4. Dorn, G. W., 2nd, Souroujon, M. C., Liron, T., Chen, C. H., Gray, M. O., Zhou, H. Z., Csukai, M., Wu, G., Lorenz, J. N., and Mochly-Rosen, D. (1999) *Proc Natl Acad Sci USA* 96, 12798-12803
5. Johnson, J. A., Gray, M. O., Chen, C. H., and Mochly-Rosen, D. (1996) *J Biol Chem* 271, 24962-24966
6. Inagaki, K., Begley, R., Ikeno, F., and Mochly-Rosen, D. (2005) *Circulation* 111, 44-50
7. Gray, M. O., Karliner, J. S., and Mochly-Rosen, D. (1997) *J Biol Chem* 272, 30945-30951
8. Lange-Asschenfeldt, C., Raval, A. P., Dave, K. R., Mochly-Rosen, D., Sick, T. J., and Perez-Pinzon, M. A. (2004) *J Cereb Blood Flow Metab* 24, 636-645
9. Malhotra, A., Begley, R., Kang, B. P., Rana, I., Liu, J., Yang, G., Mochly-Rosen, D., and Meggs, L. G. (2005) *Am J Physiol Heart Circ Physiol* 289, H 1343-1350
10. Shumilla, J. A., Liron, T., Mochly-Rosen, D., Kendig, J. J., and Sweitzer, S. M. (2005) *J Pain* 6, 535-549
11. Aley, K. O., Messing, R. O., Mochly-Rosen, D., and Levine, J. D. (2000) *J Neurosci* 20, 4680-4685
12. Tanaka, M., Terry, R. D., Mokhtari, G. K., Inagaki, K., Koyanagi, T., Kofidis, T., Mochly-Rosen, D., and Robbins, R. C. (2004) *Circulation* 110, 11194-199
13. Liu, G. S., Cohen, M. V., Mochly-Rosen, D., and Downey, J. M. (1999) *J Mol Cell Cardiol* 31, 1937-1948
14. Brodie, C., and Blumberg, P. M. (2003) *Apoptosis* 8, 19-27
15. Murriel, C. L., Churchill, E., Inagaki, K., Szweda, L. I., and Mochly-Rosen, D. (2004) *J Biol Chem* 279, 47985-47991
16. Li, W., Jiang, Y. X., Zhang, J., Soon, L., Flechner, L., Kapoor, V., Pierce, J. H., and Wang, L. H. (1998) *Mol Cell Biol* 18, 5888-5898
17. Kiley, S. C., Clark, K. J., Duddy, S. K., Welch, D. R., and Jaken, S. (1999) *Oncogene* 18, 6748-6757
18. Braun, M. U., and Mochly-Rosen, D. (2003) *J Mol Cell Cardiol* 35, 895-903
19. Morgan, A., Burgoyne, R. D., Barclay, J. W., Craig, T. J., Prescott, G. R., Ciufo, L. F., Evans, G. J., and Graham, M. E. (2005) *Biochem Soc Trans* 33, 1341-1344
20. Chen, C. H., Gray, M. O., and Mochly-Rosen, D. (1999) *Proc Natl Acad Sci USA* 96, 12784-12789
21. Inagaki, K., and Mochly-Rosen, D. (2005) *J Mol Cell Cardiol* 39, 203-211
22. Chen, L., Hahn, H., Wu, G., Chen, C. H., Liron, T., Schechtman, D., Cavallaro, G., Banci, L., Guo, Y., Bolli, R., Dorn, G. W., 2nd, and Mochly-Rosen, D. (2001) *Proc Natl Acad Sci USA* 98, 11114-11119

23. Bright, R., Raval, A. P., Dembner, J. M., Perez-Pinzon, M. A., Steinberg, G. K., Yenari, M. A., and Mochly-Rosen, D. (2004) *J Neurosci* 24, 6880-6888
24. Bright, R., and Mochly-Rosen, D. (2005) *Stroke* 36, 2781-2790
25. Newton, A. C. (2001) *Chem Rev* 101, 2353-2364
26. Kraft, A. S., Anderson, W. B., Cooper, H. L., and Sando, J. J. (1982) *J Biol Chem* 257, 13193-13196
27. Disatnik, M. H., Buraggi, G., and Mochly-Rosen, D. (1994) *Exp Cell Res* 210, 287-297
28. Churchill, E. N., Murriel, C. L., Chen, C. H., Mochly-Rosen, D., and Szweda, L. I. (2005) *Circ Res* 97, 78-85
29. Sossin, W. S., and Schwartz, J. H. (1993) *Trends Biochem Sci* 18, 207-208
30. Kohout, S. C., Corbalan-Garcia, S., Torrecillas, A., Gomez-Fernandez, J. C., and Falke, J. J. (2002) *Biochemistry* 41, 11411-11424
31. Ron, D., Luo, J., and Mochly-Rosen, D. (1995) *J Biol Chem* 270, 24180-24187
32. Zhang, Z. H., Johnson, J. A., Chen, L., El-Sherif, N., Mochly-Rosen, D., and Boutjdir, M. (1997) *Circ Res* 80, 720-729
33. Koponen, S., Kurkinen, K., Akerman, K. E., Mochly-Rosen, D., Chan, P. H., and Koistinaho, J. (2003) *J Neurochem* 86, 442-450
34. Sweitzer, S. M., Wong, S. M., Peters, M. C., Mochly-Rosen, D., Yeomans, D. C., and Kendig, J. J. (2004) *J Pharmacol Exp Ther* 309, 616-625
35. Li, H. F., Mochly-Rosen, D., and Kendig, J. J. (2005) *Br J Pharmacol* 144, 301-307
36. Sweitzer, S. M., Wong, S. M., Tjolsen, A., Allen, C. P., Mochly-Rosen, D., and Kendig, J. J. (2004) *Pain* 110, 281-289
37. Wang, J., Bright, R., Mochly-Rosen, D., and Giffard, R. G. (2004) *Neuropharmacology* 47, 136-145
38. Inagaki, K., Hahn, H. S., Dorn, G. W., 2nd, and Mochly-Rosen, D. (2003) *Circulation* 108, 869-875
39. Xiao, G. Q., Mochly-Rosen, D., and Boutjdir, M. (2003) *Biochem Biophys Res Commun* 306, 1019-1025
40. Inagaki, K., Iwanaga, Y., Sarai, N., Onozawa, Y., Takenaka, H., Mochly-Rosen, D., and Kihara, Y. (2002) *J Mol Cell Cardiol* 34, 1377-1385
41. Disatnik, M. H., Boutet, S. C., Lee, C. H., Mochly-Rosen, D., and Rando, T. A. (2002) *J Cell Sci* 115, 2151-2163
42. Schechtman, D., and Mochly-Rosen, D. (2002) *Methods Enzymol* 345, 470-489
43. Chen, L., Wright, L. R., Chen, C. H., Oliver, S. F., Wender, P. A., and Mochly-Rosen, D. (2001) *Chem Biol* 8, 1123-1129
44. Schwarze, S. R., Ho, A., Vocero-Akbani, A., and Dowdy, S. F. (1999) *Science* 285, 1569-1572
45. Khasar, S. G., Lin, Y. H., Martin, A., Dadgar, J., McMahon, T., Wang, D., Hundle, B., Aley, K. O., Isenberg, W., McCarter, G., Green, P. G., Hodge, C. W., Levine, J. D., and Messing, R. O. (1999) *Neuron* 24, 253-260
46. Disatnik, M. H., Boutet, S. C., Pacio, W., Chan, A. Y., Ross, L. B., Lee, C. H., and Rando, T. A. (2004) *J Cell Sci* 117, 4469-4479
47. Hondeghem, L. M., and Cotner, C. L. (1978) *Am J Physiol* 235, H574-580
48. Begley, R., Liron, T., Baryza, J., and Mochly-Rosen, D. (2004) *Biochem Biophys Res Commun* 318, 949-954
49. Ochoa, W. F., Garcia-Garcia, J., Fita, I., Corbalan-Garcia, S., Verdaguer, N., and Gomez-Fernandez, J. C. (2001) *J Mol Biol* 311, 837-849
50. Aderem, A. (1992) *Cell* 71, 713-716
51. Johnson, J. A., and Mochly-Rosen, D. (1995) *Circ Res* 76, 654-663
52. Stumpo, D. J., Graff, J. M., Albert, K. A., Greengard, P., and Blackshear, P. J. (1989) *Proc Natl Acad Sci USA* 86, 4012-4016
53. Critz, S. D., Cohen, M. V., and Downey, J. M. (2005) *Vascul Pharmacol* 42, 201-209
54. Vondriska, T. M., Klein, J. B., and Ping, P. (2001) *Am J Physiol Heart Circ Physiol* 280, H 1434-1441
55. Dawn, B., and Bolli, R. (2002) *Ann N Y Acad Sci* 962, 18-41
56. Saurin, A. T., Pennington, D. J., Raat, N. J., Latchman, D. S., Owen, M. J., and Marber, M. S. (2002) *Cardiovasc Res* 55, 672-680
57. Sutton, R. B., and Sprang, S. R. (1998) *Structure* 6, 1395-1405
58. Pappa, H., Murray-Rust, J., Dekker, L. V., Parker, P. J., and McDonald, N. Q. (1998) *Structure* 6, 885-894
59. Rizo, J., and Sudhof, T. C. (1998) *J Biol Chem* 273, 15879-15882
60. Allard, J. B., and Brock, T. G. (2005) *Curr Protein Pept Sci* 6, 125-131
61. Kishore, U., Gaboriaud, C., Waters, P., Shrive, A. K., Greenhough, T. J., Reid, K. B., Sim, R. B., and Arlaud, G. J. (2004) *Trends Immunol* 25, 551-561
62. Lemmon, M. A., Ferguson, K. M., and Abrams, C. S. (2002) *FEBS Lett* 513, 71-76
63. Johnson, J. A., Gray, M. O., Karliner, J. S., Chen, C. H., and Mochly-Rosen, D. (1996) *Circ. Res.* 79, 1086-99.

SUMMARY

The following aspects and embodiments thereof described and illustrated below are meant to be exemplary and illustrative, not limiting in scope.

In one aspect, a method for modulating ischemic cardiac damage in a mammalian subject is provided, comprising administering a therapeutically effective amount of a peptide comprising a contiguous amino acid sequence derived from the C2 domain of εPKC.

In some embodiments, the peptide does not include an amino acid sequence corresponding to amino acid residues 85-92 of the C2 domain of εPKC. In particular embodiments, the εPKC peptide is not ψεRACK (SEQ ID NO: 18).

In some embodiments, the εPKC peptide comprises a contiguous amino acid sequence corresponding to amino acid residues 28-35, 49-60, and 74-79, of εPKC. In some embodiments, the εPKC peptide comprises a contiguous amino acid sequence corresponding to a sequence selected from the group consisting of SEQ ID NO: 9, SEQ ID NO: 12, SEQ ID NO: 13, and SEQ ID NO: 16.

In particular embodiments, the εPKC peptide comprises a contiguous amino acid sequence corresponding to amino acid residues 28-35, 49-53, and 74-79, of εPKC. In particular embodiments, the εPKC peptide comprises a contiguous amino acid sequence corresponding to a sequence selected from the group consisting of SEQ ID NO: 9, SEQ ID NO: 12, and SEQ ID NO: 16.

In some embodiments, the εPKC peptide corresponds to the beta-sandwich region of the C2 domain of εPKC.

In some embodiments, the peptide is conjugated to a peptide that increases cellular uptake of the peptide inhibitor. In particular embodiments, the peptide that increases cellular uptake of the peptide inhibitor is TAT.

In some embodiments, the mammalian subject is a heart transplant patient.

In another aspect, an isolated peptide is provided, comprising a contiguous amino acid sequence derived from the C2 domain of a protein kinases C (PKC), wherein the peptide modulates the activity of the PKC. In some embodiments, the C2 domain of a protein kinases C (PKC) is the C2 domain of εPKC.

In some embodiments, the peptide does not include a sequence corresponding to amino acid residues 14-21 or 85-92 of the C2 domain of εPKC. In particular embodiments, the peptide is not peptide εV1-2 (SEQ ID NO: 7) or ψεRACK (SEQ ID NO: 18).

In some embodiments, the peptide is an activator of εPKC.

In some embodiments, the amino acid sequence derived from the C2 domain of a PKC corresponds to amino acid residues 28-35, 49-60, and 74-79, of εPKC. In some embodiments, the amino acid sequence derived from the C2 domain of a PKC is an amino acid sequence corresponding to a sequence selected from the group consisting of SEQ ID NO: 9, SEQ ID NO: 12, SEQ ID NO: 13, and SEQ ID NO: 16.

In particular embodiments, the amino acid sequence derived from the C2 domain of a PKC corresponds to amino acid residues 28-35, 49-53, and 74-79, of εPKC. In particular embodiments, the amino acid sequence derived from the C2 domain of a PKC is an amino acid sequence corresponding to a sequence selected from the group consisting of SEQ ID NO: 9, SEQ ID NO: 12, and SEQ ID NO: 16.

In some embodiments, the peptide reduces ischemic cardiac damage in a mammalian subject. In particular embodiments, the peptide reduces ischemic cardiac damage in a mammalian subject.

In some embodiments, the peptide is an inhibitor of εPKC.

In some embodiments, the amino acid sequence derived from the C2 domain of a PKC corresponds to amino acid residues 40-47, 62-67, and 119-124, of εPKC. In some embodiments, the amino acid sequence derived from the C2 domain of a PKC is an amino acid sequence corresponding to a sequence selected from the group consisting of SEQ ID NO: 11, SEQ ID NO: 14, and SEQ ID NO: 21.

In particular embodiments, the peptide is conjugated to a peptide that increases cellular uptake of the peptide inhibitor.

In particular embodiments, the peptide that increases cellular uptake of the peptide inhibitor is TAT.

In addition to the exemplary aspects and embodiments described above, further aspects and embodiments will become apparent by reference to the drawings and by study of the following descriptions.

DETAILED DESCRIPTION

1. Peptides Derived from the C2 Domain of εPKC

Two peptides derived from a portion of the C2 domain of εPKC were previously shown to selectively modulate εPKC activity. One peptide (εV1-2), interfered with interactions between εPKC and its anchoring protein, εRACK (5). The other peptide interfered with PKC auto-inhibitory, intramolecular interactions (4). The latter peptide was named ψεRACK because it increased PKC activity (as does binding to εRACK). It was heretofore unknown whether other regions of the C2 domain modulated PKC activity, and whether peptides with biological activity could be derived from the amino acid sequences of these regions.

The present compositions and methods are based on the identification of biologically active peptides corresponding to (i.e., derived from) amino acid sequences of the entire εPKC C2 domain (i.e., C2-derived peptides). FIGS. 1A-1D show the structure of the εC2 domain (49) in space filling (FIGS. 1A and 1B) and ribbon (FIGS. 1C and 1D) format. The numbering of the different regions in FIGS. 1C and 1D corresponds to the numbers shown in the following primary amino acid sequence of the εC2 domain (SEQ ID NO: 1).

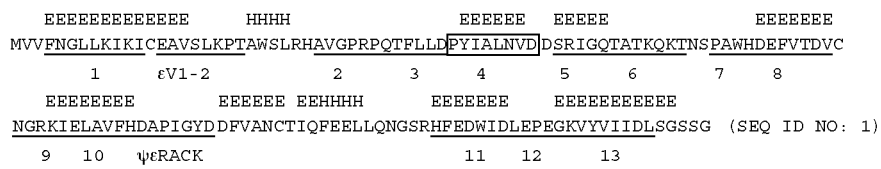

In the above sequence, "E" indicates β-strand regions and "H" indicates helical regions. Residues in unordered loop regions are shown as gaps (i.e., without E or H annotation). The underlined sequences correspond to peptides used in the present experiments. Shading and boxes represent sequences present in overlapping peptides. The location of the previously described εV1-2 and ψεRACK peptides are also indicated. Residues 1-136 of εPKC are shown. The εC2 region corresponds to residues 1-131 (i.e., Met-1 to Leu-131).

Figure 1:
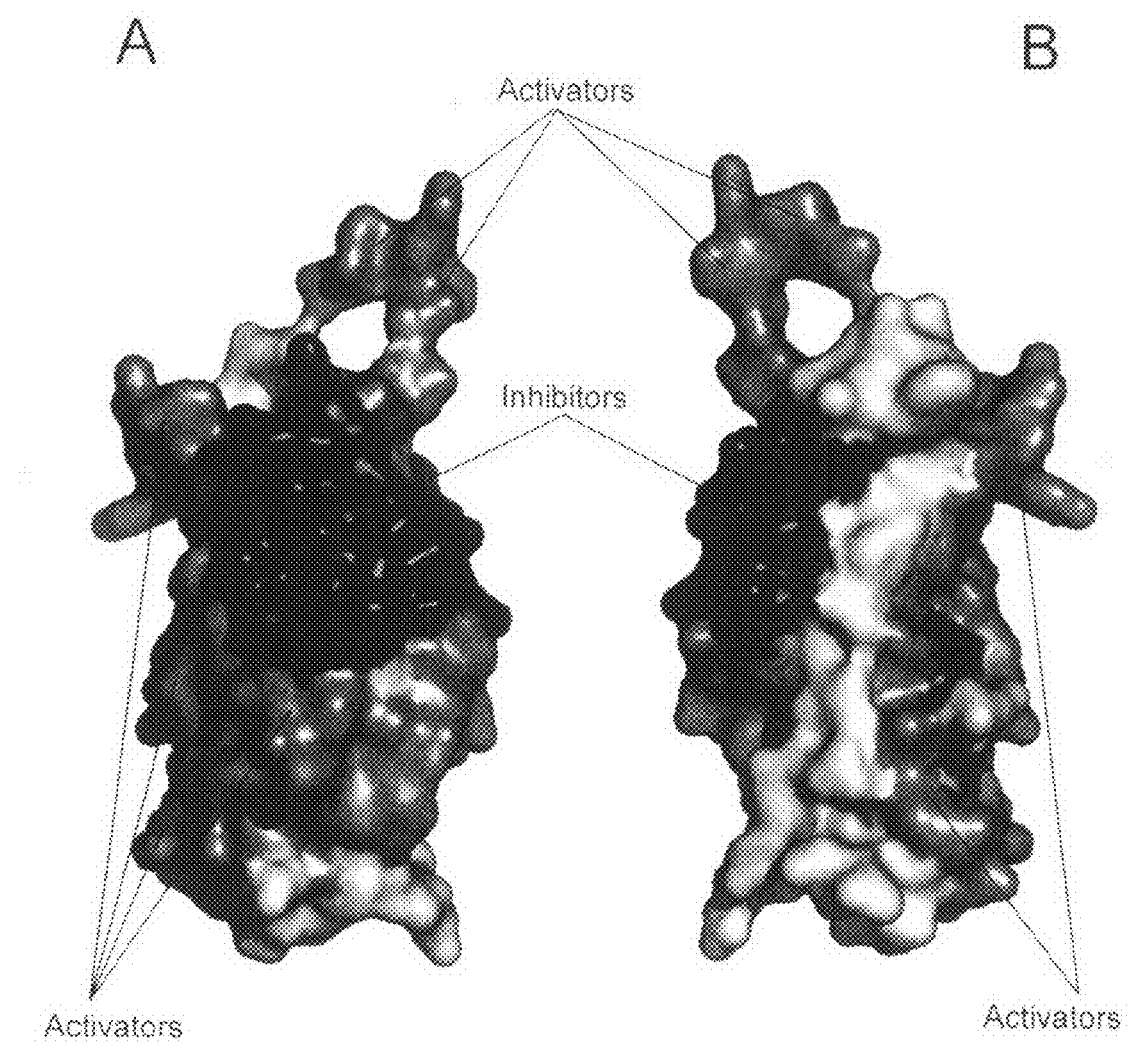
FIGS. 1A and 1B depict a space-filling model of the C2 domain of εPKC, showing surface mapping of residues based on function.
FIGS. 1C and 1D show corresponding α-carbon trace structures of the C2 domain. The structures on the right (FIGS. 1B and 1D) are rotated 180° relative to the structures on the left (FIGS. 1A and 1C).
Figure 1:
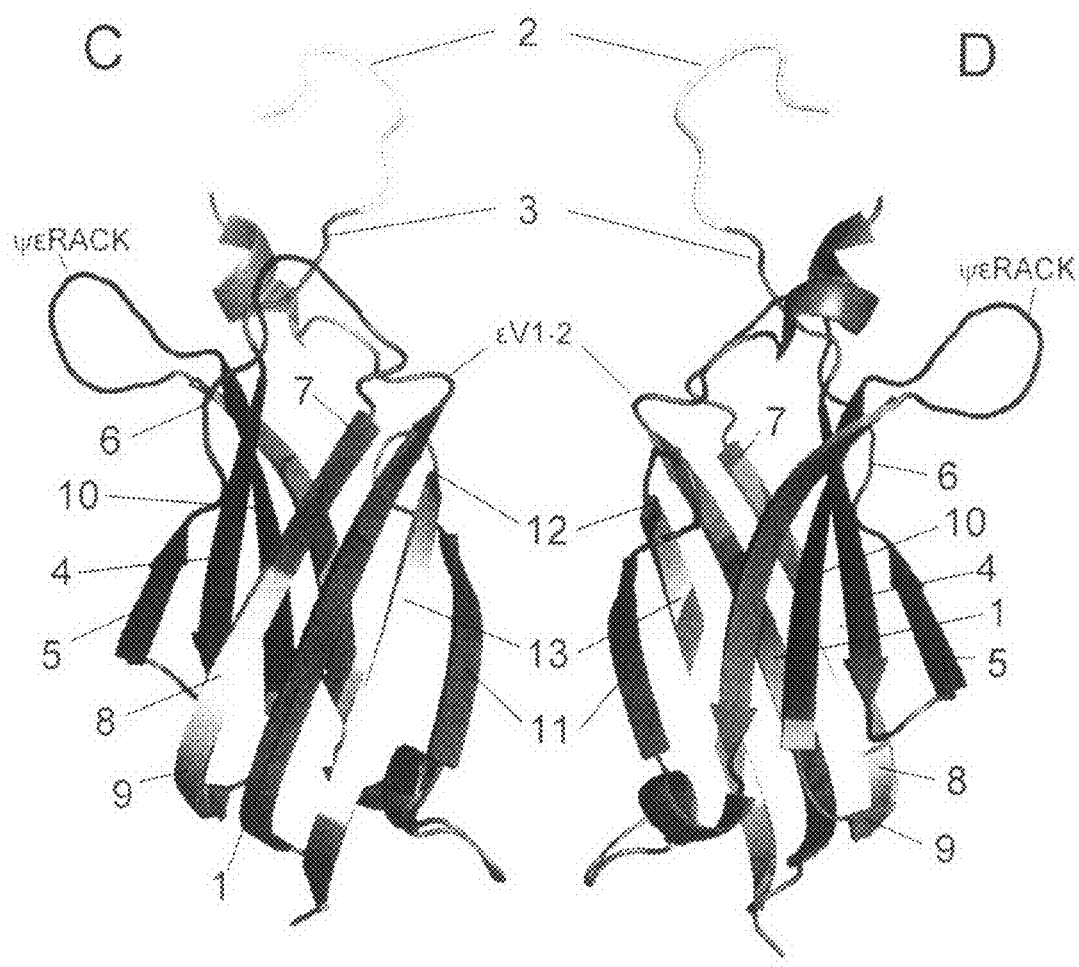

Most activating C2-derived peptides mapped to one face of the beta-sandwich (medium grey color), while three of the four inhibiting C2-derived peptides mapped to the dark grey regions (FIGS. 1A and 1B). No biologically active C2-derived peptides mapped to the light-grey regions. C2-derived peptides corresponding to regions 1, 2, 3, 5, 6, and 9, and the ΨεRACK region, were all εPKC-specific activators (FIGS.

1C and 1D). C2-derived peptides corresponding to regions 11 and 13 were non-specific PKC activators. C2-derived peptides corresponding to the εV1-2 region, and regions 4, 7, and 12, were εPKC-specific inhibitors. C2-derived peptides corresponding to regions 8 and 10 produced inconclusive results. These results are summarized in Table 1. The various peptides are described in more detail in the text and in Tables 2 and 3.

Without being limited to a theory, it is suggested that the C2 domain participates in important protein-protein interactions and that peptides derived from the C2 domain are useful for modulating intramolecular and/or intermolecular interactions with εPKC binding proteins. Peptides corresponding to regions of the C2 domain involved in intramolecular interactions with an inhibitory domain, or in intermolecular interactions with inhibitory proteins, are agonists of εPKC, as they disrupt inhibitory interactions. Peptides corresponding to binding sites for C2 activating proteins, such as εRACK, are antagonists.

Because the fold of the C2 domains of other PKC isozymes is structurally similar to that of the C2 domain of εPKC, peptides derived from homologous positions of other isozymes are likely to have similar biological activities with respect to their cognate PKC isozyme. To illustrate the homology between different PKC isozymes, an alignment of several PKC C2 domains is shown below (49,57,58). Isolated peptides shown to be isozyme-specific activators are highlighted in light grey. Isolated peptides shown to be isozyme-specific inhibitors are highlighted in dark grey. Isolated peptides shown to be non-specific activators are indicated by bold lettering.

Alignment of the C2 Domain of Several PKC Isozymes

```
              EEEEEEEEEEEE                              EEEEEE
epsil  --------------MVVFNGLLKIKICEAVSLKPTAWSLRHAVGPRPQTFLLDPYIALNVDD---------   (SEQ ID NO: 1)
eta    ----------MSSGTMKFNGYLRVRIGEAVGLQPTRWSLRHSLFKKG-HQLLDPYLTVSVDQ---------   (SEQ ID NO: 2)
delta  --------------MAPFLRISFNSYELGSLQ-------AEDEAN------QPFCAVKMKEALSTERGKT   (SEQ ID NO: 3)
alpha  HTEKRGRIYLKAEVTD---EKLHVTVRDAKNLIPMDPNGLS-----------DPYVKLKLIPDPKNES-K-   (SEQ ID NO: 4)
beta   SMERRGRIYIQAHIDR---EVLIVVVRDAKNLVPMDPNGLS-----------DPYVKLKLIPDPKSES-K-   (SEQ ID NO: 5)

EEEEE         EEEEEEE        EEEEEEE        EEEEEE EE
epsil  SRIGQTATKQKTNSPAWHDEFVTDVCNG---RKIELAVFH-DAPIGYDDFVANCTIQFEELLQN--GSR
eta    VRVGQTSTKQKTNKPTYNEEFCANVTDG---GHLELAVFH-ETPLGYD-FVANCTLQFQELVGTTGASD
delta  --LVQKKPTM---YPEWKSTFDAHIYEG---RVIQIVLMRAAE----EPMSEVTVGVSVLAERCKKNNG
alpha  ---QKTKTIRSTLNPQWNESFTFKLKPSDKDRRLSVEIWDWDRTTRNDFMGSLSFGVSELMKMP-----
beta   ---QKTKTIKCSLNPEWNETFRFQLKESDKDRRLSVEIWDWDLTSRNDFMGSLSFGISELQKAG-----

EEEEEEE               EEEEEEEEEEE
epsil  HFEDWIDLEPE--------------GKVYVIIDLSGSSG
eta    TFEGWVDLEPE--------------GKVFVVITLT----
delta  KAEFWLDLQPQ--------------AKVLMSVQYFLED-
alpha  AS-GWYKLLNQEEGEYYNVPIPEG GRIYLKAEV
beta   V-DGWFKLLSQEEGEYFNVP     GRIYIQAHI
```

Since homologs of the C2 domain are present in over 60 different proteins (59), many of which are signaling proteins, the results of the present study are also likely to apply to proteins other than PKC, including but not limited to 5-lipoxygenase (60), pleckstrin (61), and members of the tumor necrosis factor family (62).

Experiments performed in support of the present peptides and methods are described, below.

TABLE 1

The biological activities of the εPKC C2-derived peptides and controls used in the study.

| Peptide | εPKC translocation in cells | MARCKS phosphorylation in WT Cells | MARCKS phosphorylation in εKO Cells | Cardio-protective ex vivo | PKC translocation, in vivo |
|---|---|---|---|---|---|
| 2 | activator | activator | no effect | yes | NT[a] |
| 5 | activator | activator | no effect | yes | activates ε and not δ α, ζPKC |
| 6 | activator | activator | weak activator | yes | NT[a] |
| 9 | activator | activator, | no effect | yes | NT[a] |
| ψεRACK | activator | activator | no effect | yes | activates and not δ α, ζPKC |
| 1 | activator | activator | no effect | yes† | activates ε and not δ α, ζPKC |

TABLE 1-continued

The biological activities of the ePKC C2-derived peptides and controls used in the study.

| Peptide | ePKC translocation in cells | MARCKS phosphorylation in WT Cells | MARCKS phosphorylation in eKO Cells | Cardio-protective ex vivo | PKC translocation, in vivo |
|---------|-----|-----|-----|-----|-----|
| 3 | activator | activator | no effect | yes‡ | $NT^a$ |
| 8 | activator | not conclusive | not conclusive | no | $NT^a$ |
| 10 | activator | activator | not conclusive | no | $NT^a$ |
| 11 | trend towards activator | activator | activator | no | non specific; activates ε, α, and δPKC |
| 13 | activator | activator | activator | no | $NT^a$ |
| εV1-2 | inhibitor | inhibitor | no effect | no | Inhibits only $ePKC^b$ |
| 4 | inhibitor | inhibitor | $NT^a$ | $NT^a$ | $NT^a$ |
| 7 | inhibitor | inhibitor | $NT^a$ | no | $NT^a$ |
| 12 | inhibitor | inhibitor | $NT^a$ | $NT^a$ | $NT^a$ |
| scrambled εV1-2 | activator | no effect | no effect | no | no |
| scrambled ψεRACK | $NT^a$ | $NT^a$ | $NT^a$ | no | $NT^a$ |
| TAT carrier | no effect | no effect | no effect | no | $NT^a$ |

$^a$NT—not tested
$^a$Previous study (48)
†trend towards cardioprotective (n = 5)
‡trend towards cardioprotective (n = 3)

II. Experiments Performed in Support of the Invention

Thirteen 5-9-residue peptides derived from amino sequences that span the C2 domain (also known as the V1 domain (29); residues 1-131) of εPKC were synthesized and tested for their ability to modulate εPKC activation using several in vitro and in vivo biological assays. In addition to the indicated C2-derived peptides, three peptides were synthesized as controls, in particular, scrambled versions of a previously established peptide activator (ψεRACK) and inhibitor (εV1-2), and the TAT carrier peptide alone. As previously described, these peptides were introduced into cells as "cargo" by conjugating them to a cell-penetrating "carrier" peptide (i.e., $TAT_{47-57}$) (43,44). Tables 2 and 3 lists all the peptides tested in experiments in support of the present peptides and methods, including the amino acid sequences, SEQ ID NOs, and corresponding region of the C2 (V1) domain.

Four assays were used to investigate the effect of the TAT-conjugated peptides on εPKC: (i) εPKC translocation in cultured cells (26), (ii) phosphorylation of the PKC substrate MARCKS in cultured cells (41,50), (iii) a cardiac protection assay (4,6,7) carried out using an intact heart, ex vivo, and (iv) in vivo translocation of PKC after a single intraperitoneal injection (48).

A. εPKC Translocation in Cells

Upon activation, PKC translocates from the soluble to the particulate cell fraction, which translocation can be monitored by immunoblot analysis (26). It was previously determined that the effect of peptides on PKC translocation is better observed when the cells are treated with a sub-maximal concentration of PMA (22,42). Larger concentrations of PMA, a non-physiological activator, stimulate a greater degree of PKC translocation over translocation stimulated by peptide activators alone (51). PKC translocation upon peptide treatment, although less than that seen with large amounts of PMA, has been shown to better correlate with other experimental data (4,6,22)).

Pre-treatment with most peptides prior to PMA-stimulation increased the amount of εPKC in the pellet fraction and a decreased the amount in the soluble fraction, indicating that the peptides stimulated (activated) εPKC translocation. FIG. 2A shows representative immunoblot analyses and accompanying graphs of the data. A representative activator (peptide 2) or inhibitor (peptide 7) were preincubated at 500 nM for 15 minutes with cells before sub-optimal stimulation with 3 nM PMA for 7 minutes.

TABLE 2

TAT-conjugated peptides εPKC C2-derived peptides and controls used in the study assays.

| Peptide | Primary Sequence | SEQ ID NO: | Origin of Sequence |
|---------|------------------|------------|--------------------|
| 1 | $\underline{C}FNGLLKIKI^a$ | 6 | $eC2/V1_{4-12}$ |
| $eV1-2^b$ | $\underline{C}EAVSLKPT^a$ | 7 | $eC2/V1_{14-21}$ |
| scrambled $eV1-2^d$ | $\underline{C}LSETKPAV^a$ | 8 | scrambled $eC2/V1_{14-21}$ |
| 2 | $\underline{C}AVGPRPQT^a$ | 9 | $eC2/V1_{28-35}$ |
| 3 | $\underline{C}FLLDPY^a$ | 10 | $eC2/V1_{36-41}$ |
| 4 | $\underline{C}PYIALNVD^a$ | 11 | $eC2/V1_{40-47}$ |
| 5 | $\underline{C}SRIGQ^a$ | 12 | $eC2/V1_{49-53}$ |
| 6 | $\underline{C}TATKQKT^a$ | 13 | $eC2/V1_{54-60}$ |
| 7 | $\underline{C}PAWHD^a$ | 14 | $eC2/V1_{62-67}$ |
| 8 | $\underline{C}EFVTDV^a$ | 15 | $eC2/V1_{68-73}$ |
| 9 | $\underline{C}NGRKI^a$ | 16 | $eC2/V1_{74-79}$ |

TABLE 2-continued

TAT-conjugated peptides εPKC C2-derived peptides and controls used in the study assays.

| Peptide | Primary Sequence | SEQ ID NO: | Origin of Sequence |
|---|---|---|---|
| 10 | <u>C</u>IELAVF[a] | 17 | εC2/V1$_{79-84}$ |
| ψεRACK[c] | <u>C</u>HDAPIGYD[a] | 18 | εC2/V1$_{85-92}$ |
| scrambled ψεRACK[d] | <u>C</u>PDYHDAGI[a] | 19 | scrambled εC2/V1$_{85-92}$ |
| 11 | <u>C</u>HFEDWID[a] | 20 | εC2/V1$_{112-118}$ |
| 12 | <u>C</u>LEPEGK[a] | 21 | εC2/V1$_{119-124}$ |
| 13 | <u>C</u>VYVIIDL[a] | 22 | εC2/V1$_{125-131}$ |
| TAT carrier[d] | <u>C</u>YGRKKRRQRRR | 23 | TAT$_{47-57}$ |

[a]Peptides conjugated by Cys (underlined) S—S bond to TAT$_{47-57}$ carrier peptide.
[b]Previously published εPKC-specific inhibitor, εV1-2 (5).
[c]Previously published εPKC-specific activator, ψεRACK (4).
[d]Used as a control peptide; corresponds to SEQ ID NO: 31 with an additional, N-terminal C.

TABLE 3

Additional peptides with known PKC-modulating activity

| Peptide | Isozyme | Sequence† | SEQ ID NO: | Activity | Ref. |
|---|---|---|---|---|---|
| ψβRACK | βPKC | SVEIWD | 24 | activate all the classical PKC isozymes | (31) |
| βC2-4 | βPKC | SLNPEWNET | 25 | inhibit of all the classical PKC isozymes | (31) |
| βC2-2 | βPKC | MDPNGLSDPYVKL | 26 | inhibit of all the classical PKC isozymes | (31) |
| δψRACK | δPKC | MRAAEDPM | 27 | agonist, selective for δPKC | (22) |
| δV1-1 | δPKC | SFNSYELGSL | 28 | antagonist, selective for δPKC | (22) |
| — | ηPKC | EAVGLQPT | 29 | inhibitor | (1, 63) |
| — | ηPKC | HETPLGYD | 30 | activator | (1, 63) |

†Shown without the additional N-terminal C residue used for conjugation.

Pretreatment with peptide 2 increased the amount of εPKC translocation by approximately 30% compared to pre-treatment with the TAT control peptide (n=5, p<0.05). Pretreatment with peptide 7 decreased the amount of translocated εPKC by approximately 50% compared to pre-treatment with the TAT control peptide (n=3, p<0.01). Statistical significance was determined by Students t-Test using Microsoft Excel.

The histogram shown in FIG. 2B summarizes the effects of the various peptides on εPKC translocation in cells. As noted above, increased translocation indicates activation of PKC, while decrease translocation indicates inhibition. All the peptides altered εPKC translocation. Pre-treatment with four peptides, i.e., peptides 4, 7, 12, and εV1-2 (which was previously reported to be an εPKC-selective inhibitor) before PMA stimulation resulted in a decrease in the amount of εPKC in the pellet fraction relative to control, indicating that these peptides may act as inhibitors of εPKC translocation. The scrambled εV1-2 peptide (LSETKPAV)) also stimulated εPKC translocation in CHO cells, although this result was not apparent from other assays described, herein. Pre-treatment with TAT carrier peptide alone had no effect on PKC translocation. All data were statistically significant (n>3, p<0.05), as determined by Students t-Test using Microsoft Excel.

B. PKC Substrate Phosphorylation in Cells

While translocation is a rapid and convenient in vitro assay, it is not strictly indicative of PKC activation (26). A more direct and sensitive measure of PKC activation is PKC substrate phosphorylation. Because there are no known εPKC-specific substrates, myristoylated alanine-rich C kinase substrate (MARCKS) was used. MARCKS is a widely distributed actin cross-linking protein that is highly phosphorylated on serine residues (50,52) following PKC activation.

The level of MARCKS phosphorylation was determined using antibodies specific for phosphorylated MARCKS, following incubation of primary mouse muscle cells from wildtype (WT, FIGS. 3A and 3C) or εPKC knock-out (KO, FIG. 3B) mice with 1 μM each peptide for 15 minutes (FIGS. 3A and 3B) or 30 minutes (FIG. 3C) prior to cell lysis. This assay has been used before to show that integrin-induced ε, α and δPKC activation leads to MARCKS phosphorylation (41). The data shown are from several experiments (indicated in each column) and statistical significance was determined by Student's t-Test using Microsoft Excel.

Dark gray bars indicate no significant difference compared to control; light gray bars in FIG. 3B indicate a trend towards an effect that was not statistically significant; white bars indicate a significant effect. Actin was used as a loading control. In total, 11 of the peptides increased MARCKS phosphorylation compared to no peptide treatment or TAT-control treatment (FIG. 3A and Table 2), indicating that these peptides were PKC activators. No change in MARCKS phosphorylation was observed following treatment with the control peptides scrambled εV1-2 or scrambled ψεRACK. Only peptide 8 had no conclusive effect on MARCKS phosphorylation.

The availability of εPKC-knock out (KO) mice and cells derived therefrom, increased the utility of the MARCKS phosphorylation assay. Changes in the levels of phosphorylated MARCKS in cells obtained from both WT and εPKC KO mice indicated that the effects of the TAT-conjugated peptides were not selective for εPKC. However, changes only in cells obtained from WT mice indicated that the effects of the TAT-conjugated peptides were specific to the εPKC isozyme Most of the peptides (six out of eleven activators: peptides 1, 2, 3, 5, 9, and ψεRACK) increased MARCKS phosphorylation in WT but not in KO muscle cells and are therefore εPKC-selective activators (FIGS. 3A and 3B, Table 2). A few peptides increased MARCKS phosphorylation (e.g., peptides 11 and 13) in both cell types and are therefore not specific for εPKC. In no case did a peptide affect MARCKS phosphorylation in KO and not WT cells. The MARCKS phosphorylation assay was primarily used to show a gain of function (i.e., PKC activation); nonetheless, peptides 4, 7, 12, and εV1-2 inhibited MARCKS phosphorylation in WT cells.

This phosphorylation assay suggested that several peptides derived from the C2 domain of εPKC affected the activity of PKC, and that a subset of these peptides were isozyme-selective.

C. Ex Vivo Cardiac Protection

An ex vivo model of ischemia and reperfusion (47) was used to further characterize the C2-derived peptides. Studies have demonstrated that activation of εPKC in hearts prior to an ischemic event leads to reduced damage of the myocardium (4,7,53-55). Pre-treatment of hearts subjected to ischemia and reperfusion ex vivo (using a Langendorff apparatus) with the ψεRACK peptide led to reduced damage (infarction) (4,43). Because other PKC isozymes have no effect on cardiac protection (e.g., βPKC (43)), or even have opposing effects to εPKC activation (e.g., δPKC activation increases damage (22)), changes in cardiac protection following perfusion with a εC2-derived peptide indicates only εPKC modulation.

FIGS. 4A and 4B show analyses of the effects of C2 derived peptides in an ex vivo model of ischemia and reperfusion. FIG. 4A shows representative cross-sections of treated and control hearts stained with 2,3,5-triphenyltetrazolium chloride (TTC) to assess tissue infarction. Live tissue stained darkly, while dead tissue remained white. FIG. 4B shows quantitation of infarct size based on the staining. The data are an average of several experiments (indicated in each column) and statistical significance was determined by Student's t-Test using Microsoft Excel. Bar shading is the same as in FIG. 3. With the exception of peptide εV1-2, none of the peptides that demonstrated inhibitory activity in the translocation or MARCKS phosphorylation assays (i.e., peptides 4, 7 and 12) were tested in the ex vivo assay.

Based on the level of damage observed by TTC staining (FIG. 4A) and release of CPK (a cytosolic enzyme that is released from the myocytes when the muscle is damaged; FIG. 4B), it was concluded that peptides 2, 5, 6, and 9, as well as the previously characterized εPKC-selective agonist, ψεRACK, were cardioprotective, indicating that these peptides are εPKC-selective activators. Peptides 1 and 3 showed a trend towards cardioprotection, but the data were not statistically significant. The four peptides that did not induce MARCKS phosphorylation in WT and KO skeletal muscle cells, i.e., peptide 8, and the three control peptides (scrambled εV1-2, scrambled ψεRACK, and TAT), were not cardioprotective. Peptides 11 and 13, which induced MARCKS phosphorylation in both WT and KO cells were also not cardioprotective, possibly because in addition to εPKC they activate the opposing isozyme δPKC (22). Note that treatment with peptide 9 involved hearts subjected to only 30 minutes of ischemia instead of 40 minutes. These results of the ex vivo cardiac protection assay are summarized in Table 2.

D. In Vivo PKC Translocation

In a further in vivo study, peptide activity and selectivity were examined using representative peptides injected into mice via intraperitoneal (IP) injection, and the amount of εPKC, δPKC, αPKC, and ζPKC translocation in hearts was determined. These four PKC isozymes represent each of the three major sub-families of PKC. In particular, εPKC and δPKC are members of the novel PKC family (calcium insensitive, diacylglycerol sensitive), αPKC is a classical PKC (calcium and diacylglycerol sensitive), and ζPKC is an atypical PKC (calcium and diacylglycerol insensitive). A previous study demonstrated the effects of PKC regulating peptides on PKC translocation in hearts and other organs after a single intraperitoneal injection (48).

Levels of εPKC, δPKC, αPKC, and ζPKC in the particulate fraction of mouse hearts were assayed by immunoblot 15 minutes following IP injection of 20 nmol each peptides (FIGS. 5A-5D). The accompanying graphs show quantitation based on two experiments, calculated as fold increase (+/− standard error) in the particulate fraction/total fraction, normalized to the actin loading control, and relative to the control TAT peptide. The ψεRACK peptide, peptide 1, and peptide 5 caused translocation of εPKC, but not δPKC, ζPKC, or αPKC, indicating that these peptides were selective εPKC activators. Since peptides 11 and 13 caused MARCKS phosphorylation in myocytes from the εPKC knockout mice (FIG. 3), it is concluded that they activated several PKC isozymes. Further, because these peptides did not protect the heart from ischemic damage, it is believed that they activate both the cardiac protective isozyme, εPKC (4,22,56), and one or more isozymes that mediates cardiac damage, such as δPKC (22, 38). IP injection of peptide 11 caused a substantial translocation of δPKC, αPKC, and εPKC (FIG. 5C), consistent with other observations suggesting that peptide 11 is a promiscuous activator of PKC.

Atypical ζPKC, present only in the soluble cell fraction, did not translocate in response to any peptide tested (FIG. 5D). Control peptide (scrambled εV1-2) did not cause an increase in either εPKC or δPKC (FIG. 5C).

E. Summary of Results

Figure 2:
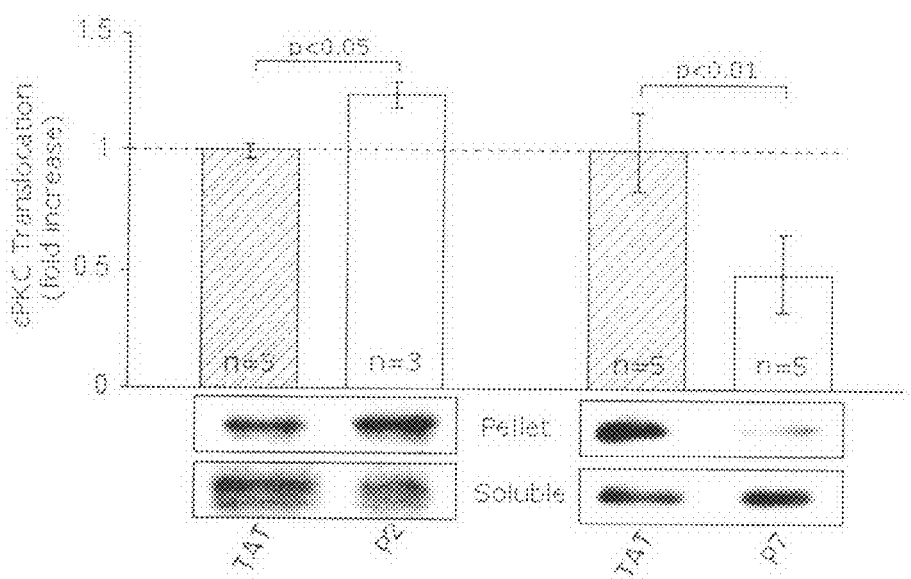
FIGS. 2A shows immunoblot analyses and resulting graphs of εPKC translocation in cells.
FIG. 2B shows a histogram summarizing the effects of various peptides on εPKC translocation in cells.
Figure 2:
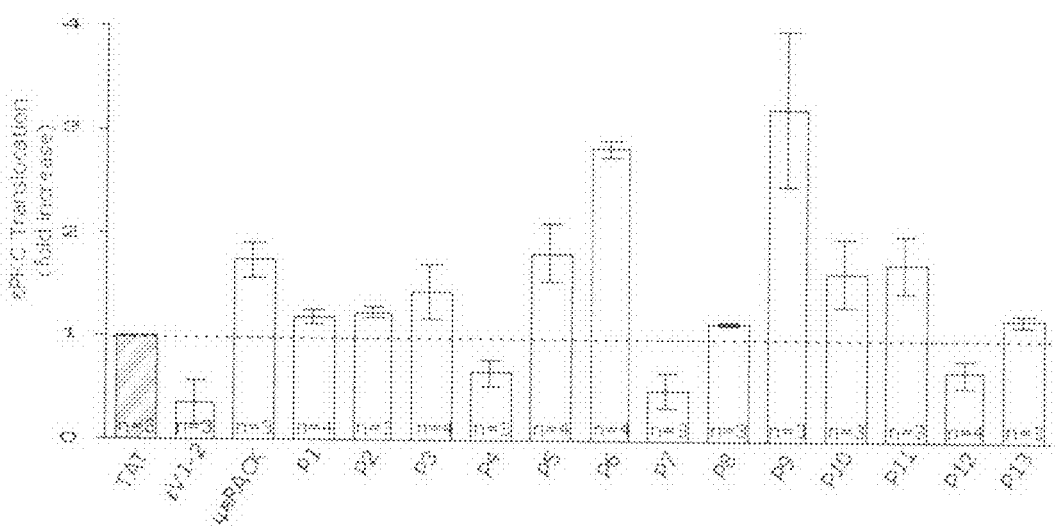
Figure 3:
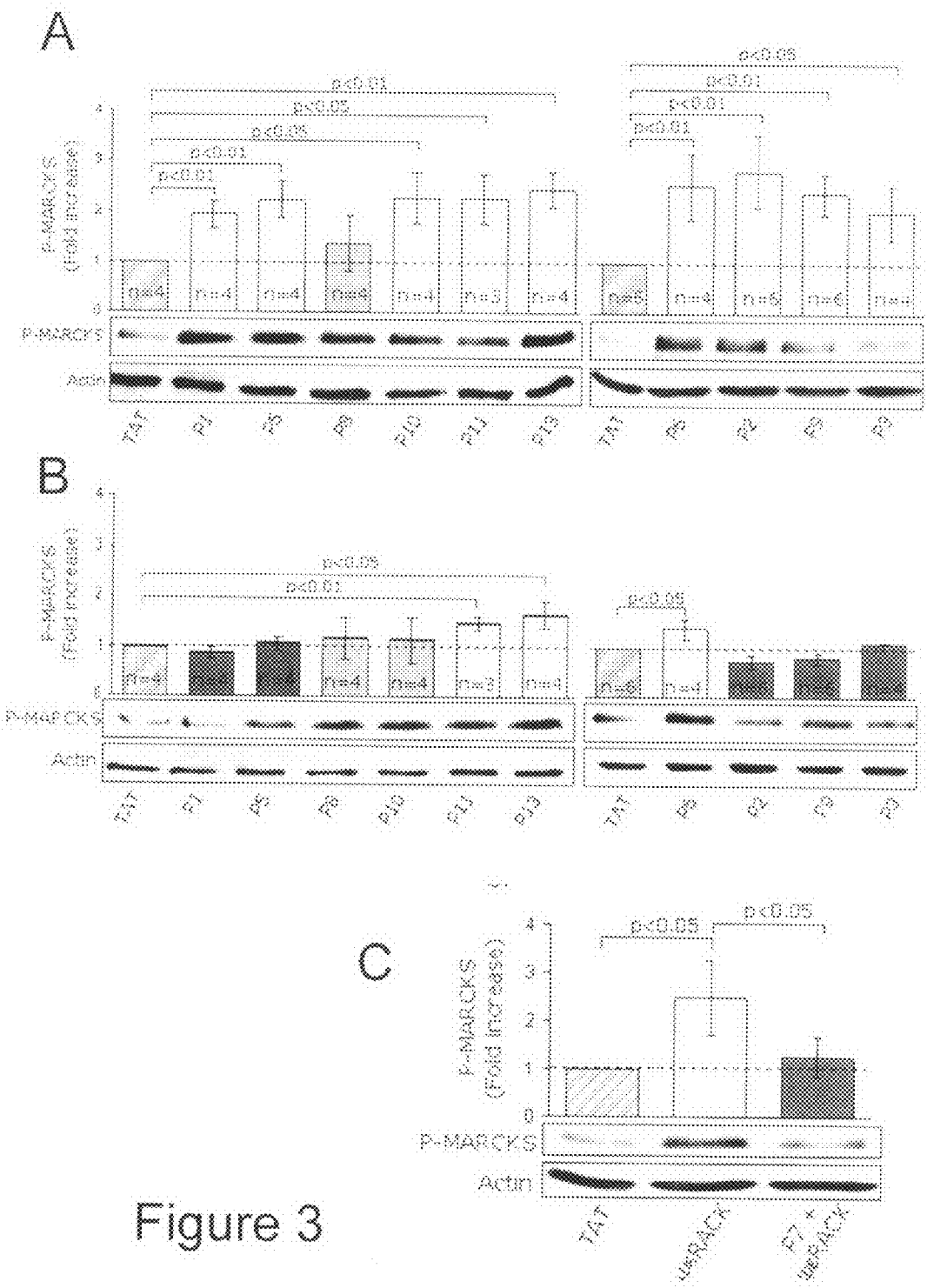
FIGS. 3A-3C show analyses of the effects of C2 derived peptides on MARCKS phosphorylation in primary muscle cells.
Figure 4:
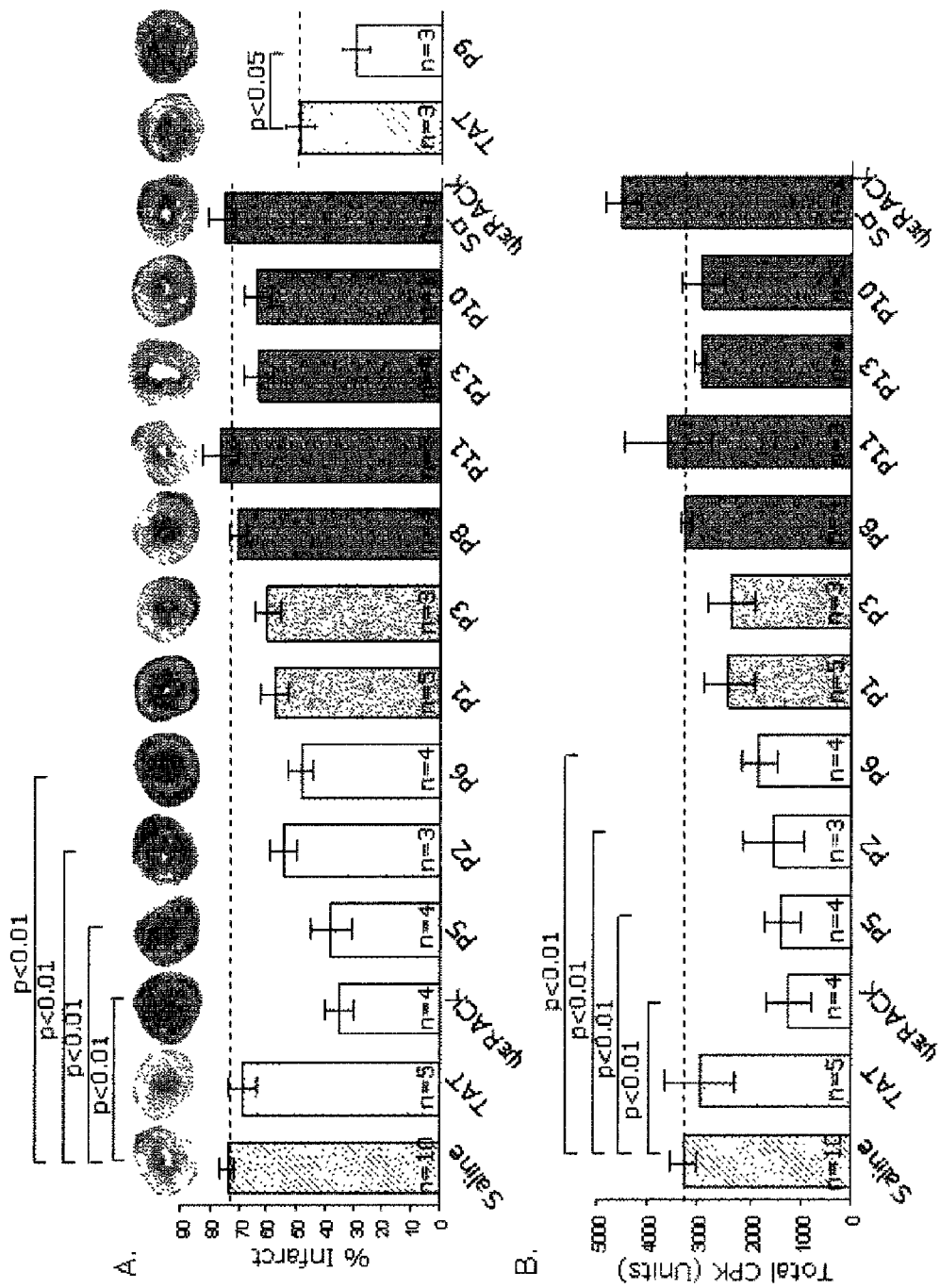
FIGS. 4A and 4B show analyses of the effects of C2 derived peptides in an ex vivo model of ischemia and reperfusion. (A) Cross-sections of treated and control hearts stained with TTC to assess tissue infarction. (B) Graph showing relative infarct size based on staining.

The peptides tested in the above experiments encompassed almost all the β-sheet regions and parts of the top and bottom loop regions of the εC2 domain (FIGS. 1A-1D). The biological activity of each peptide is shown in Table 1. All the peptides derived from the C2 domain of εPKC modulated the activity of εPKC in the two cell-based assays (i.e., translocation and MARCKS phosphorylation; FIGS. 2 and 3). Of these, 10 peptides were εPKC activators (peptides 1, 2, 3, 5, 6, 9, 10, ψεRACK, 11, and 13) as demonstrated by an increase in εPKC translocation and an increase in MARCKS phosphorylation. These peptides correspond to εPKC residues 4-12, 28-41, 49-60, 74-92, 112-118, and 125-131. Five peptides that activated εPKC in the two cell-based assays were cardioprotective, i.e., peptides 2, 5, 6, 9, and ψεRACK, corresponding to εPKC residues 28-35, 49-60, 74-79, and 85-92; FIG. 4. Of these five peptides, four (peptides 2, 5, 9, and ψεRACK; i.e., residues 28-35, 49-53, 74-79, and 85-92) were selective for εPKC as determined by MARCKS phosphorylation using cells obtained from WT or εPKC KO mice (FIG. 3).

Figure 5:
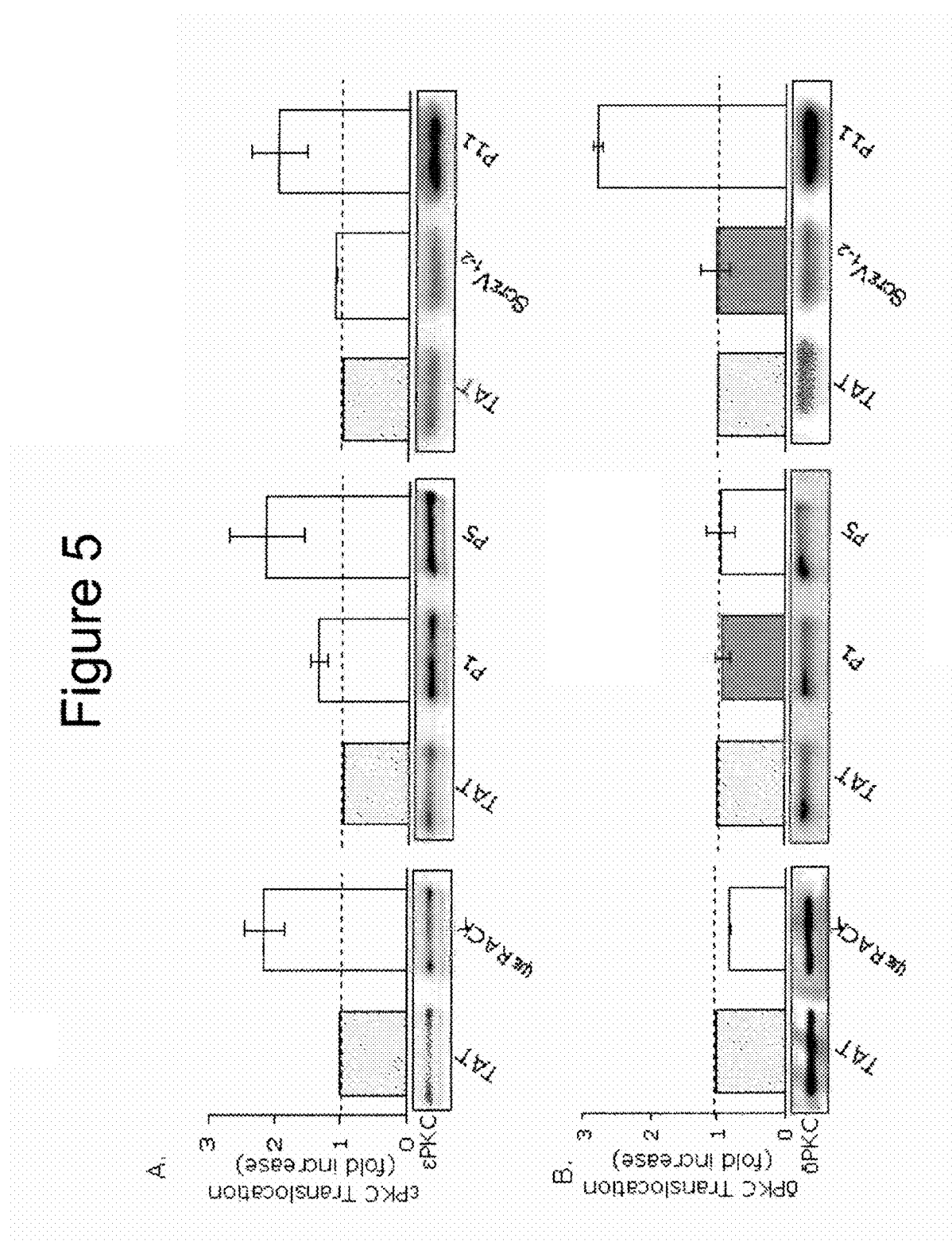
FIGS. 5A-5D show immunoblot analyses and resulting graphs of εPKC translocation in heart tissue following in vivo treatment with C2-derived peptides from εPKC (A), δPKC (B), αPKC (C), and ζPKC (D).
Figure 5:
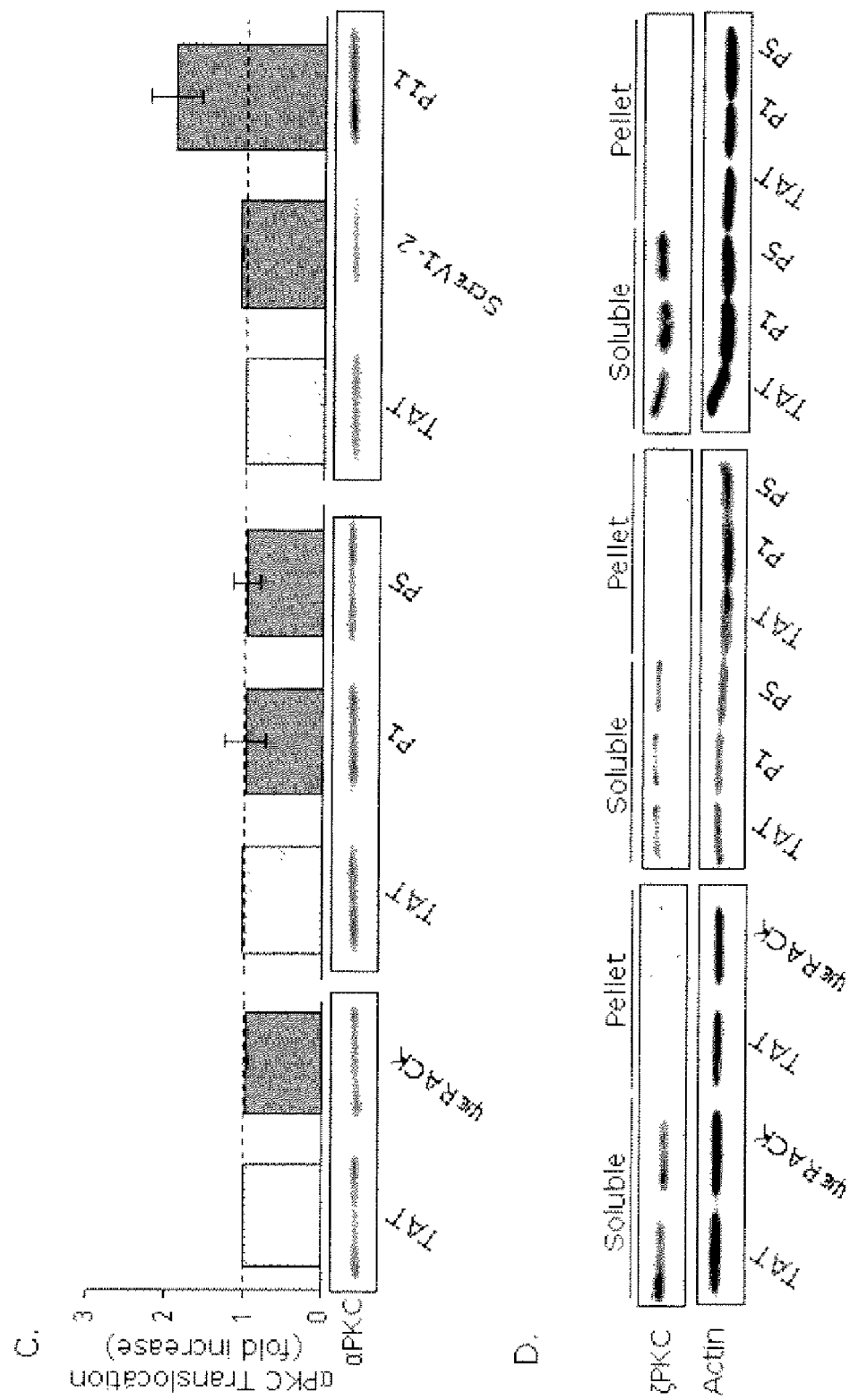

Two of the peptides (peptides 11 and 13) activated PKC in vitro but were not selective for εPKC (FIGS. 2 and 3). These peptides correspond to εPKC residues 112-118 and 125-131. The two peptides did not induce cardiac protection from ischemia and reperfusion (FIG. 4), suggesting that they affect PKC isozymes (e.g., δPKC) that increases cardiac damage by ischemia (22). Translocation studies in vivo confirmed that peptide 11 activated δ and εPKC as well as αPKC (FIG. 5).

Four peptides (peptides εV1-2, 4, 7, and 12) were εPKC inhibitors (FIGS. 2 and 3). These peptides correspond to εPKC residues 14-21, 40-47, 62-67, and 119-124.

Together, these results demonstrate the ability of εC2 domain-derived peptides to modulate εPKC biological activity as activators or inhibitors, depending on the particular region of the C2 domain represented by the peptide.

III. Treatment Methods

The data described herein show that activator peptides derived from the C2 region of εPKC are cardioprotective in an animal model for ischemic heart damage. Such peptides are useful for slowing or inhibiting the progression of heart failure following ischemia, prolonging survival, reducing fractional shortening, reducing left ventricular weight to body weight ratio, reducing fibrosis, causing the EKG/ECG of a subject to more closely resemble that of a healthy animal, and/or combinations thereof. The peptides may be of particular value in protecting a heart from ischemic damage during a transplantation procedure.

C2-derived peptides for administration to humans or other animals (preferably mammals) may include natural amino acids, such as the L-amino acids or non-natural amino acids, such as D-amino acids. The amino acids in the peptide may be linked by peptide bonds or, in modified peptides described herein, by non-peptide bonds. A wide variety of modifications to the amide bonds which link amino acids may be made and are known in the art. Such modifications are discussed in general reviews (e.g., Freidinger, R. M. (2003) *J. Med. Chem.* 46:5553; Ripka, A. S. and Rich, D. H. (1998) *Curr. Opin. Chem. Biol.* 2:441). These modifications are designed to improve the properties of the peptide by increasing the potency of the peptide or by increasing the half-life of the peptide.

The potency of the peptide may be increased by restricting conformational flexibility. This may be achieved by, for example, including the placement of additional alkyl groups on the nitrogen or alpha-carbon of the amide bond, such as the peptoid strategy of Zuckerman et al. and the alpha modifications of Goodman et. al. (see, e.g., (1996) *Pure Appl. Chem.* 68:1303). The amide nitrogen and alpha carbon may be linked together to provide additional constraint (Scott et al. (2004) *Org. Letts.* 6:1629-32).

The half-life of the peptide may be increased by introducing non-degradable moieties to the peptide chain. This may be achieved by, for example, replacement of the amide bond by a urea residue (Patil et al. (2003) *J. Org. Chem.* 68:7274-80) or an aza-peptide link (Zega and Urleb (2002) *Acta Chim. Slov.* 49:649-62). Other examples of non-degradable moieties that may be introduced to the peptide chain include introduction of an additional carbon "beta peptide" (Gellman, S. H. (1998) *Acc. Chem. Res.* 31:173) or ethene unit (Hagihara et al. (1992) *J. Am. Chem. Soc.* 114:6568) to the chain, or the use of hydroxyethylene moieties (Patani, G. A. and Lavoie, E. J. (1996) *Chem. Rev.* 96:3147-76) and are also well known in the art. Additionally, one or more amino acids may be replaced by an isosteric moiety such as, for example, the pyrrolinones of Hirschmann et al ((2000) *J. Am. Chem. Soc.* 122:11037), or tetrahydropyrans (Kulesza, A. et al. (2003) *Org. Letts.* 5:1163). A common modification to increase half-life is pegylation.

Although the peptides are described primarily with reference to amino acid sequences from *Rattus norvegicus*, it is understood that the peptides are not limited to the specific amino acid sequences set forth herein. Skilled artisans will recognize that, through the process of mutation and/or evolution, polypeptides of different lengths and having different constituents, e.g., with amino acid insertions, substitutions, deletions, and the like, may arise that are related to, or sufficiently similar to, a sequence set forth herein by virtue of amino acid sequence homology and advantageous functionality as described herein.

The peptides described herein encompass amino acid sequences similar to the amino acid sequences set forth herein that have at least about 50% identity thereto and function in a similar manner. Preferably, the amino acid sequences have at least about 60% identity, at least about 70% identity, at least about 80% identity, at least about 90% identity, or at least about 95% identity to described sequences. Exemplary percent identity values are at least about 90%, 91%, 92%, 93%, 94%, 95%, 96%, 97%, 98%, and 99%. Percent identity may be determined, for example, by comparing sequence information using the advanced BLAST computer program, including version 2.2.9, available from the National Institutes of Health. The BLAST program is based on the alignment method of Karlin and Altschul. ((1990) *Proc. Nat'l. Acad. Sci. U.S.A.* 87:2264-68) and as discussed in Altschul et al. ((1990) *J. Mol. Biol.* 215:403-10); Karlin and Altschul ((1993) *Proc. Nat'l. Acad. Sci. U.S.A.* 90:5873-77); and Altschul et al. ((1997) *Nucleic Acids Res.* 25:3389-3402).

Conservative amino acid substitutions may be made in the amino acid sequences to obtain derivatives of the peptides that may advantageously be utilized in the present invention. Conservative amino acid substitutions, as known in the art and as referred to herein, involve substituting amino acids in a protein with amino acids having similar side chains in terms of, for example, structure, size and/or chemical properties. For example, the amino acids within each of the following groups may be interchanged with other amino acids in the same group: amino acids having aliphatic side chains, including glycine, alanine, valine, leucine and isoleucine; amino acids having non-aromatic, hydroxyl-containing side chains, such as serine and threonine; amino acids having acidic side chains, such as aspartic acid and glutamic acid; amino acids having amide side chains, including glutamine and asparagine; basic amino acids, including lysine, arginine and histidine; amino acids having aromatic ring side chains, including phenylalanine, tyrosine and tryptophan; and amino acids having sulfur-containing side chains, including cysteine and methionine. Additionally, aspartic acid, glutamic acid and their amides, are also considered interchangeable herein.

In some embodiments, the C2-derived peptide is conjugated to a cell permeable carrier protein or peptide that may increase cellular uptake of the peptide inhibitor. In one example, a *Drosophila* Antennapedia homeodomain-derived sequence (CRQIKIWFQNRRMKWKK; SEQ ID NO: 32), is attached (i.e., conjugated) to the C2-derived peptide by cross-linking via an N-terminal Cys-Cys bond as discussed in Theodore, L. et al. ((1995) *J. Neurosci.* 15:7158-67) and Johnson, J. A. et al. ((1996) *Circ. Res* 79:1086). In some embodiments, the C2-derived peptides are conjugated to cell permeable carrier peptides between cysteine residues on the amino or carboxy-termini of the peptides. Such cysteine residues may be part of the naturally-occurring peptide sequence or may be added to the naturally-occurring peptide sequence.

The present peptides were modified by a Transactivating Regulatory Protein (Tat)-derived transport polypeptide (such as from amino acids 47-57 of Tat (YGRKKRRQRRR; SEQ ID NO: 31) from the Human Immunodeficiency Virus, Type 1, as described in Vives et al. ((1997) *J. Biol. Chem.*, 272: 16010-17), U.S. Pat. No. 5,804,604, and Genbank Accession No. AAT48070; or with polyarginine as described in Mitchell et al. ((2000) *J. Peptide Res.* 56:318-25) and Rothbard et al. (2000) *Nature Med.* 6:1253-57). Such TAT derived cell permeable carrier peptides may be conjugated to C2-derived peptides between cysteine residues, as described immediately above.

C2-derived peptides having both PKC sequences and cell permeable carrier peptide sequences, with or without additional cysteine residues, may also be synthesized using standard methods, e.g., to produce a single peptide having both inhibitor peptide and cell permeable carrier peptide sequences. C2-derived peptides may be modified by other methods known to the skilled artisan in order to increase the cellular uptake of the peptides.

The C2-derived peptides may be advantageously administered in various forms. For example, the C2-derived peptides may be administered in tablet form for sublingual administration, in a solution or emulsion. The C2-derived peptides may also be mixed with a pharmaceutically-acceptable carrier or vehicle. The vehicle may be a liquid, suitable, for example, for parenteral administration, including water, saline or other aqueous solution, or may be an oil or aerosol. The carrier may be selected for intravenous or intraarterial administration, and may include a sterile aqueous or non-aqueous solution that may include preservatives, bacteriostats, buffers and antioxidants known to the art. In the aerosol form, the inhibitor may be used as a powder, with properties including particle size, morphology and surface energy known to the art for optimal dispersability. In tablet form, a solid carrier may include, for example, lactose, starch, carboxymethyl cellulose, dextrin, calcium phosphate, calcium carbonate, synthetic or natural calcium allocate, magnesium oxide, dry aluminum hydroxide, magnesium stearate, sodium bicarbonate, dry yeast or a combination thereof. The tablet preferably includes one or more agents which aid in oral dissolution. The C2-derived peptides may also be administered in forms in which other similar drugs known in the art are administered.

The C2-derived peptides may be administered to a patient by a variety of routes. For example, the peptides may be administered parenterally, including intraperitoneally, intravenously, intraarterially, subcutaneously, or intramuscularly. The C2-derived peptides may also be administered via a mucosal surface, including rectally, and intravaginally; intranasally, including by inhalation; sublingually; intraocularly and transdermally. Combinations of these routes of administration are also envisioned. A preferred mode of administration is by infusion or reperfusion through an artery, or an artery that is connected to such an occluded or partially-occluded artery. By "partially-occluded artery" it is meant herein an artery in which blood flow is reduced after an ischemic attack or other hypoxic event affecting the heart blood vessels when compared to blood flow prior to such event or attack.

In certain embodiments, C2-derived peptides may be co-administered in a composition with a second therapeutic agent. In this manner, one skilled in the art will recognize that C2-derived peptides individually, in combination, or combined with a second therapeutic agent, may be used to prepare a medicament for the slowing or inhibiting the progression of ischemic heart failure.

Further aspects and embodiments will be apparent to the skilled artisan in view of the present teachings. The foregoing description and the following examples are not intended to be limiting.

EXAMPLES

Experimental Procedures

Peptide Synthesis—Peptides were synthesized and conjugated to TAT carrier peptide (residues 47-57) via cysteine S—S bond by Anaspec, San Jose, Calif. Peptides are five to eight residues and represent sequences in the C2/V1 domain of εPKC. Three control peptides have also been synthesized: scrambled εV1-2, scrambled εψRACK, and TAT carrier peptide alone. See Table 1 for a summary of peptides synthesized, including sequences.

PKC Translocation in Cells—εPKC translocation from the soluble to the particulate fraction in CHO cells was used to assess the relative amount of activated (membrane-bound) εPKC, an assay that has been described previously (42). Evidence of translocation is either by an increase in the amount of PKC in the particulate fraction or by a decrease in the soluble fraction. Briefly, after stimulation, cells were washed with cold PBS, scraped in homogenization buffer, passed through a (25G⅝") syringe needle, and spun at 100,000 g for 30 min at 4° C. The pellet was then resuspended in homogenization buffer with 1% Triton X-100. Where applicable, the cells were pre-incubated with 500 nM peptide for 15 minutes prior to stimulation. PKC was stimulated with sub-maximal levels of the general PKC activator phorbol 12-myristate 13-acetate (PMA, 3 nM). The samples were then analyzed by Western blot. Antibodies against εPKC were obtained from Santa Cruz Biotechnology (Santa Cruz, Calif.) and used at 1:500 dilution. Antibodies against actin, used as a loading control, were obtained from Sigma-Aldrich (St. Louis, Mo.) and used at 1:1000 dilution.

PKC Substrate Phosphorylation in Cells—Phosphorylation of myristoylated alanine-rich C kinase substrate (MARCKS), a general PKC substrate, was monitored by Western blot of cell lysates. To assess PKC activation by the peptides and their specificity for εPKC, MARCKS phosphorylation in wild-type primary skeletal muscle cells was compared with MARCKS phosphorylation in primary skeletal muscle cells isolated from εPKC knockout mice (45), as we previously described (46). Primary skeletal muscle cells were prepared as previously published (46). εKO cells were prepared from εPKC knockout mice (45). For the εPKC inhibition assay, WT cells were treated with 1 μM peptide 7 for 15 minutes and then ψεRACK (500 nM) was added for 30 minutes prior to cell lysis. Antibodies against phosphorylated MARCKS were obtained from Cell Signaling (Danvers, Mass.) and used at 1:500 dilution. Antibodies against actin, used as a loading control, were obtained from Sigma-Aldrich (St. Louis, Mo.) and used at 1:1000 dilution.

Ex Vivo Cardiac Protection—Activation of εPKC prior to ischemia mediates cardiac protection in an ex vivo model of acute ischemic heart damage (13), an assay that has been described previously (47). Briefly, Wistar rats (300 to 350 g) were heparinized (1000 U/kg IP) and then anesthetized with sodium pentobarbital (100 mg/kg IP). Hearts were rapidly excised and then perfused with an oxygenated Krebs-Henseleit buffer containing NaCl (120 mmol/L), KCl (5.8 mmol/L), NaHCO3 (25 mmol/L), Nash 2PO4 (1.2 mmol/L), MgSO4 (1.2 mmol/L), CaCl2 (1.0 mmol/L), and dextrose (10 mmol/L) at pH 7.4 and 37° C. in a Langendorff coronary perfusion system. A constant coronary flow rate of 10 mL/min was used. Hearts were submerged into a heat-jacketed organ bath at 37° C. Coronary effluent was collected to determine creatine phosphokinase (CPK) release. After 10 minutes of equilibration, the hearts were subjected to 40 minutes global ischemia and 60 minutes reperfusion. The hearts were perfused with 1 μM TAT-conjugated peptide for 10 minutes prior to ischemia. In addition to the relative amount of CPK released, a measure of cardiac myocyte lysis, tissue damage was assessed by triphenyl tetrazolium chloride (TTC) staining of heart cross-sections to quantitate the amount of infarcted (dead) tissue, as we previously described (38).

Isozyme Selectivity In Vivo—To determine that activator peptides causing MARCKS phosphorylation and decreasing ischemia-reperfusion damage in heart also induce εPKC translocation in vivo, we injected the respective peptides at 20 nmol in 200 μl saline into the peritoneum of 15-20 g mice, as previously reported (48). Fifteen minutes later, the mice were sacrificed and heart and brain were collected. Soluble and particulate fractions from mouse tissue were prepared as previously described (48). ε, ζ and δPKC translocation were determined by Western blot analysis using selective anti-PKC antibodies from Santa Cruz Biotechnology, Santa Cruz, Calif. and used at 1:500 dilution. Sarcomeric actin (1:1000, Sigma) was used as a loading control for all fractions.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. An isolated peptide between five and nine amino acid residues in length consisting of an amino acid sequence having at least 90% sequence identity to a contiguous amino acid sequence of SEQ ID NO:1, wherein the peptide does not comprise a sequence corresponding to amino acid residues 14-21 or 85-92 of SEQ ID NO:1, and wherein the peptide modulates the activity of εPKC.

2. The peptide of claim 1, wherein the peptide is an activator of εPKC.

3. The peptide of claim 2, wherein the amino acid sequence corresponds to amino acid residues 28-35 of SEQ ID NO:1.

4. The peptide of claim 2, wherein the amino acid sequence corresponds to amino acid residues 28-35, 49-60, 49-53, or 74-79 of SEQ ID NO:1.

5. The peptide of claim 1, wherein the peptide reduces ischemic cardiac damage in a mammalian subject.

6. The peptide of claim 1, wherein the peptide is an inhibitor of εPKC.

7. The peptide of claim 6, wherein the amino acid sequence corresponds to amino acid residues 40-47, 62-67, or 119-124 of SEQ ID NO:1.

8. An isolated peptide consisting of
(a) a first amino acid sequence between five and nine amino acids in length having at least 90% sequence identity to a contiguous amino acid sequence of SEQ ID NO:1, wherein the peptide does not comprise a sequence corresponding to amino acid residues 14-21 or 85-92 of SEQ ID NO:1, and
(b) a terminal cysteine residue,
wherein the peptide modulates the activity of εPKC.

9. The peptide of claim 8, wherein the peptide does not consist of the sequence of SEQ ID NO:7 or SEQ ID NO:18.

10. The peptide of claim 8, wherein the peptide is SEQ ID NO:9.

11. The peptide of claim 8, wherein the peptide reduces ischemic cardiac damage in a mammalian subject.

12. The peptide of claim 8, wherein the amino acid sequence is selected from the group consisting of SEQ ID NO: 11, SEQ ID NO: 14, and SEQ ID NO: 21.

13. The peptide of claim 8, wherein the peptide is conjugated to a carrier peptide.

14. The peptide of claim 13, wherein the carrier peptide comprises SEQ ID NO:31 or SEQ ID NO:32.

15. The peptide of claim 13, wherein the peptide is cross-linked to the carrier peptide by an N-terminal Cys-Cys bond.

16. The peptide of claim 8, wherein the first amino acid sequence corresponds to amino acid residues 28-35, 49-60, 49-53, or 74-79 of SEQ ID NO:1.

17. The peptide of claim 8, wherein said peptide consists of SEQ ID NO:9.

18. The peptide of claim 8, wherein the peptide is an activator of εPKC.

19. A conjugate comprising,
(a) a first peptide consisting of
(1) an amino acid sequence between five and nine amino acids in length and having at least 90% sequence identity to a contiguous amino acid sequence of SEQ ID NO:1, wherein the amino acid sequence does not comprise a sequence corresponding to amino acid residues 14-21 or 85-92 of SEQ ID NO:1, and
(2) a terminal cysteine residue,
wherein the first peptide modulates the activity of εPKC; and
(b) a carrier peptide,
wherein the first peptide and the carrier peptide are attached.

20. The conjugate of claim 19, wherein the first peptide and the carrier peptide are attached by cross-linking via an N-terminal Cys-Cys bond.

21. The conjugate of claim 19, wherein the carrier peptide comprises SEQ ID NO:31 or SEQ ID NO:32.

22. The conjugate of claim 19, wherein the first peptide consists of SEQ ID NO:9.

* * * * *

SEQUENCE LISTING

```
<160> NUMBER OF SEQ ID NOS: 32

<210> SEQ ID NO 1
<211> LENGTH: 136
<212> TYPE: PRT
<213> ORGANISM: Artificial Sequence
<220> FEATURE:
<223> OTHER INFORMATION: epsilon PKC C2 domain

<400> SEQUENCE: 1

Met Val Val Phe Asn Gly Leu Leu Lys Ile Lys Ile Cys Glu Ala Val
 1               5                  10                  15

Ser Leu Lys Pro Thr Ala Trp Ser Leu Arg His Ala Val Gly Pro Arg
            20                  25                  30

Pro Gln Thr Phe Leu Leu Asp Pro Tyr Ile Ala Leu Asn Val Asp Asp
        35                  40                  45

Ser Arg Ile Gly Gln Thr Ala Thr Lys Gln Lys Thr Asn Ser Pro Ala
    50                  55                  60

Trp His Asp Glu Phe Val Thr Asp Val Cys Asn Gly Arg Lys Ile Glu
65                  70                  75                  80

Leu Ala Val Phe His Asp Ala Pro Ile Gly Tyr Asp Asp Phe Val Ala
                85                  90                  95

Asn Cys Thr Ile Gln Phe Glu Glu Leu Leu Gln Asn Gly Ser Arg His
            100                 105                 110

Phe Glu Asp Trp Ile Asp Leu Glu Pro Glu Gly Lys Val Tyr Val Ile
        115                 120                 125

Ile Asp Leu Ser Gly Ser Ser Gly
    130                 135

<210> SEQ ID NO 2
<211> LENGTH: 136
<212> TYPE: PRT
<213> ORGANISM: Artificial Sequence
<220> FEATURE:
<223> OTHER INFORMATION: eta PKC C2 domain

<400> SEQUENCE: 2

Met Ser Ser Gly Thr Met Lys Phe Asn Gly Tyr Leu Arg Val Arg Ile
 1               5                  10                  15

Gly Glu Ala Val Gly Leu Gln Pro Thr Arg Trp Ser Leu Arg His Ser
```

-continued

```
                    20                  25                  30
Leu Phe Lys Lys Gly His Gln Leu Leu Asp Pro Tyr Leu Thr Val Ser
            35                  40                  45
Val Asp Gln Val Arg Val Gly Gln Thr Ser Thr Lys Gln Lys Thr Asn
 50                  55                  60
Lys Pro Thr Tyr Asn Glu Glu Phe Cys Ala Asn Val Thr Asp Gly Gly
 65                  70                  75                  80
His Leu Glu Leu Ala Val Phe His Glu Thr Pro Leu Gly Tyr Asp Phe
                85                  90                  95
Val Ala Asn Cys Thr Leu Gln Phe Gln Glu Leu Val Gly Thr Thr Gly
            100                 105                 110
Ala Ser Asp Thr Phe Glu Gly Trp Val Asp Leu Glu Pro Glu Gly Lys
        115                 120                 125
Val Phe Val Val Ile Thr Leu Thr
    130                 135

<210> SEQ ID NO 3
<211> LENGTH: 124
<212> TYPE: PRT
<213> ORGANISM: Artificial Sequence
<220> FEATURE:
<223> OTHER INFORMATION: delta PKC C2 domain

<400> SEQUENCE: 3

Met Ala Pro Phe Leu Arg Ile Ser Phe Asn Ser Tyr Glu Leu Gly Ser
 1               5                  10                  15
Leu Gln Ala Glu Asp Glu Ala Asn Gln Pro Phe Cys Ala Val Lys Met
            20                  25                  30
Lys Glu Ala Leu Ser Thr Glu Arg Gly Lys Thr Leu Val Gln Lys Lys
        35                  40                  45
Pro Thr Met Tyr Pro Glu Trp Lys Ser Thr Phe Asp Ala His Ile Tyr
    50                  55                  60
Glu Gly Arg Val Ile Gln Ile Val Leu Met Arg Ala Ala Glu Glu Pro
 65                  70                  75                  80
Met Ser Glu Val Thr Val Gly Val Ser Val Leu Ala Glu Arg Cys Lys
                85                  90                  95
Lys Asn Asn Gly Lys Ala Glu Phe Trp Leu Asp Leu Gln Pro Gln Ala
            100                 105                 110
Lys Val Leu Met Ser Val Gln Tyr Phe Leu Glu Asp
        115                 120

<210> SEQ ID NO 4
<211> LENGTH: 148
<212> TYPE: PRT
<213> ORGANISM: Artificial Sequence
<220> FEATURE:
<223> OTHER INFORMATION: alpha PKC C2 domain

<400> SEQUENCE: 4

His Thr Glu Lys Arg Gly Arg Ile Tyr Leu Lys Ala Glu Val Thr Asp
 1               5                  10                  15
Glu Lys Leu His Val Thr Val Arg Asp Ala Lys Asn Leu Ile Pro Met
            20                  25                  30
Asp Pro Asn Gly Leu Ser Asp Pro Tyr Val Lys Leu Lys Leu Ile Pro
        35                  40                  45
Asp Pro Lys Asn Glu Ser Lys Gln Lys Thr Lys Thr Ile Arg Ser Thr
    50                  55                  60
```

```
Leu Asn Pro Gln Trp Asn Glu Ser Phe Thr Phe Lys Leu Lys Pro Ser
 65                  70                  75                  80

Asp Lys Asp Arg Arg Leu Ser Val Glu Ile Trp Asp Trp Asp Arg Thr
                 85                  90                  95

Thr Arg Asn Asp Phe Met Gly Ser Leu Ser Phe Gly Val Ser Glu Leu
            100                 105                 110

Met Lys Met Pro Ala Ser Gly Trp Tyr Lys Leu Leu Asn Gln Glu Glu
        115                 120                 125

Gly Glu Tyr Tyr Asn Val Pro Ile Pro Glu Gly Arg Ile Tyr Leu
    130                 135                 140

Lys Ala Glu Val
145

<210> SEQ ID NO 5
<211> LENGTH: 144
<212> TYPE: PRT
<213> ORGANISM: Artificial Sequence
<220> FEATURE:
<223> OTHER INFORMATION: beta PKC C2 domain

<400> SEQUENCE: 5

Ser Met Glu Arg Arg Gly Arg Ile Tyr Ile Gln Ala His Ile Asp Arg
 1               5                  10                  15

Glu Val Leu Ile Val Val Arg Asp Ala Lys Asn Leu Val Pro Met
                 20                  25                  30

Asp Pro Asn Gly Leu Ser Asp Pro Tyr Val Lys Leu Lys Leu Ile Pro
            35                  40                  45

Asp Pro Lys Ser Glu Ser Lys Gln Lys Thr Lys Thr Ile Lys Cys Ser
 50                  55                  60

Leu Asn Pro Glu Trp Asn Glu Thr Phe Arg Phe Gln Leu Lys Glu Ser
 65                  70                  75                  80

Asp Lys Asp Arg Arg Leu Ser Val Glu Ile Trp Asp Trp Asp Leu Thr
                 85                  90                  95

Ser Arg Asn Asp Phe Met Gly Ser Leu Ser Phe Gly Ile Ser Glu Leu
            100                 105                 110

Gln Lys Ala Gly Val Asp Gly Trp Phe Lys Leu Leu Ser Gln Glu Glu
        115                 120                 125

Gly Glu Tyr Phe Asn Val Pro Gly Arg Ile Tyr Ile Gln Ala His Ile
    130                 135                 140

<210> SEQ ID NO 6
<211> LENGTH: 10
<212> TYPE: PRT
<213> ORGANISM: Artificial Sequence
<220> FEATURE:
<223> OTHER INFORMATION: epsilon C2/V1(4-12)

<400> SEQUENCE: 6

Cys Phe Asn Gly Leu Leu Lys Ile Lys Ile
 1               5                  10

<210> SEQ ID NO 7
<211> LENGTH: 9
<212> TYPE: PRT
<213> ORGANISM: Artificial Sequence
<220> FEATURE:
<223> OTHER INFORMATION: epsilon V1-2

<400> SEQUENCE: 7

Cys Glu Ala Val Ser Leu Lys Pro Thr
```

-continued

```
1               5

<210> SEQ ID NO 8
<211> LENGTH: 9
<212> TYPE: PRT
<213> ORGANISM: Artificial Sequence
<220> FEATURE:
<223> OTHER INFORMATION: scrambled epsilon V1-2 peptide

<400> SEQUENCE: 8

Cys Leu Ser Glu Thr Lys Pro Ala Val
1               5

<210> SEQ ID NO 9
<211> LENGTH: 9
<212> TYPE: PRT
<213> ORGANISM: Artificial Sequence
<220> FEATURE:
<223> OTHER INFORMATION: epsilon C2/V1(28-35)

<400> SEQUENCE: 9

Cys Ala Val Gly Pro Arg Pro Gln Thr
1               5

<210> SEQ ID NO 10
<211> LENGTH: 7
<212> TYPE: PRT
<213> ORGANISM: Artificial Sequence
<220> FEATURE:
<223> OTHER INFORMATION: epsilon C2/V1 (36-41)

<400> SEQUENCE: 10

Cys Phe Leu Leu Asp Pro Tyr
1               5

<210> SEQ ID NO 11
<211> LENGTH: 9
<212> TYPE: PRT
<213> ORGANISM: Artificial Sequence
<220> FEATURE:
<223> OTHER INFORMATION: epsilon C2/V1(40-47)

<400> SEQUENCE: 11

Cys Pro Tyr Ile Ala Leu Asn Val Asp
1               5

<210> SEQ ID NO 12
<211> LENGTH: 6
<212> TYPE: PRT
<213> ORGANISM: Artificial Sequence
<220> FEATURE:
<223> OTHER INFORMATION: epsilon C2/V1(49-53)

<400> SEQUENCE: 12

Cys Ser Arg Ile Gly Gln
1               5

<210> SEQ ID NO 13
<211> LENGTH: 8
<212> TYPE: PRT
<213> ORGANISM: Artificial Sequence
<220> FEATURE:
<223> OTHER INFORMATION: epsilon C2/V1(54-60)

<400> SEQUENCE: 13

Cys Thr Ala Thr Lys Gln Lys Thr
1               5
```

-continued

<210> SEQ ID NO 14
<211> LENGTH: 6
<212> TYPE: PRT
<213> ORGANISM: Artificial Sequence
<220> FEATURE:
<223> OTHER INFORMATION: epsilon C2/V1(62-67)

<400> SEQUENCE: 14

Cys Pro Ala Trp His Asp
1               5

<210> SEQ ID NO 15
<211> LENGTH: 7
<212> TYPE: PRT
<213> ORGANISM: Artificial Sequence
<220> FEATURE:
<223> OTHER INFORMATION: epsilon C2/V1(68-73)

<400> SEQUENCE: 15

Cys Glu Phe Val Thr Asp Val
1               5

<210> SEQ ID NO 16
<211> LENGTH: 6
<212> TYPE: PRT
<213> ORGANISM: Artificial Sequence
<220> FEATURE:
<223> OTHER INFORMATION: epsilon C2/V1(74-79)

<400> SEQUENCE: 16

Cys Asn Gly Arg Lys Ile
1               5

<210> SEQ ID NO 17
<211> LENGTH: 7
<212> TYPE: PRT
<213> ORGANISM: Artificial Sequence
<220> FEATURE:
<223> OTHER INFORMATION: epsilon C2/V1(79-84)

<400> SEQUENCE: 17

Cys Ile Glu Leu Ala Val Phe
1               5

<210> SEQ ID NO 18
<211> LENGTH: 9
<212> TYPE: PRT
<213> ORGANISM: Artificial Sequence
<220> FEATURE:
<223> OTHER INFORMATION: pseudoepsilon RACK peptide

<400> SEQUENCE: 18

Cys His Asp Ala Pro Ile Gly Tyr Asp
1               5

<210> SEQ ID NO 19
<211> LENGTH: 9
<212> TYPE: PRT
<213> ORGANISM: Artificial Sequence
<220> FEATURE:
<223> OTHER INFORMATION: scrambled pseudoepsilon RACK peptide

<400> SEQUENCE: 19

Cys Pro Asp Tyr His Asp Ala Gly Ile
1               5

<210> SEQ ID NO 20
<211> LENGTH: 8
<212> TYPE: PRT
<213> ORGANISM: Artificial Sequence
<220> FEATURE:
<223> OTHER INFORMATION: epsilon C2/V1(112-118)

<400> SEQUENCE: 20

Cys His Phe Glu Asp Trp Ile Asp
 1               5

<210> SEQ ID NO 21
<211> LENGTH: 7
<212> TYPE: PRT
<213> ORGANISM: Artificial Sequence
<220> FEATURE:
<223> OTHER INFORMATION: epsilon C2/V1(119-124)

<400> SEQUENCE: 21

Cys Leu Glu Pro Glu Gly Lys
 1               5

<210> SEQ ID NO 22
<211> LENGTH: 8
<212> TYPE: PRT
<213> ORGANISM: Artificial Sequence
<220> FEATURE:
<223> OTHER INFORMATION: epsilon C2/V1(125-131)

<400> SEQUENCE: 22

Cys Val Tyr Val Ile Ile Asp Leu
 1               5

<210> SEQ ID NO 23
<211> LENGTH: 12
<212> TYPE: PRT
<213> ORGANISM: Artificial Sequence
<220> FEATURE:
<223> OTHER INFORMATION: TAT carrier peptide with N-terminal cysteine

<400> SEQUENCE: 23

Cys Tyr Gly Arg Lys Lys Arg Arg Gln Arg Arg Arg
 1               5                  10

<210> SEQ ID NO 24
<211> LENGTH: 6
<212> TYPE: PRT
<213> ORGANISM: Artificial Sequence
<220> FEATURE:
<223> OTHER INFORMATION: pseudobetaRACK peptide

<400> SEQUENCE: 24

Ser Val Glu Ile Trp Asp
 1               5

<210> SEQ ID NO 25
<211> LENGTH: 9
<212> TYPE: PRT
<213> ORGANISM: Artificial Sequence
<220> FEATURE:
<223> OTHER INFORMATION: beta C2-4 peptide

<400> SEQUENCE: 25

Ser Leu Asn Pro Glu Trp Asn Glu Thr
 1               5

-continued

```
<210> SEQ ID NO 26
<211> LENGTH: 13
<212> TYPE: PRT
<213> ORGANISM: Artificial Sequence
<220> FEATURE:
<223> OTHER INFORMATION: beta C2-2 peptide

<400> SEQUENCE: 26

Met Asp Pro Asn Gly Leu Ser Asp Pro Tyr Val Lys Leu
 1               5                  10

<210> SEQ ID NO 27
<211> LENGTH: 8
<212> TYPE: PRT
<213> ORGANISM: Artificial Sequence
<220> FEATURE:
<223> OTHER INFORMATION: deltapseudoRACK peptide

<400> SEQUENCE: 27

Met Arg Ala Ala Glu Asp Pro Met
 1               5

<210> SEQ ID NO 28
<211> LENGTH: 10
<212> TYPE: PRT
<213> ORGANISM: Artificial Sequence
<220> FEATURE:
<223> OTHER INFORMATION: peptide delta V1-1

<400> SEQUENCE: 28

Ser Phe Asn Ser Tyr Glu Leu Gly Ser Leu
 1               5                  10

<210> SEQ ID NO 29
<211> LENGTH: 8
<212> TYPE: PRT
<213> ORGANISM: Artificial Sequence
<220> FEATURE:
<223> OTHER INFORMATION: peptide derived from eta PKC

<400> SEQUENCE: 29

Glu Ala Val Gly Leu Gln Pro Thr
 1               5

<210> SEQ ID NO 30
<211> LENGTH: 8
<212> TYPE: PRT
<213> ORGANISM: Artificial Sequence
<220> FEATURE:
<223> OTHER INFORMATION: peptide derived from eta PKC

<400> SEQUENCE: 30

His Glu Thr Pro Leu Gly Tyr Asp
 1               5

<210> SEQ ID NO 31
<211> LENGTH: 11
<212> TYPE: PRT
<213> ORGANISM: Artificial Sequence
<220> FEATURE:
<223> OTHER INFORMATION: TAT carrier protein

<400> SEQUENCE: 31

Tyr Gly Arg Lys Lys Arg Arg Gln Arg Arg Arg
 1               5                  10

<210> SEQ ID NO 32
```

```
<211> LENGTH: 17
<212> TYPE: PRT
<213> ORGANISM: Artificial Sequence
<220> FEATURE:
<223> OTHER INFORMATION: Antennapedia homeodomain peptide

<400> SEQUENCE: 32

Cys Arg Gln Ile Lys Ile Trp Phe Gln Asn Arg Arg Met Lys Trp Lys
 1               5                  10                  15

Lys
```